US012708461B2

(12) United States Patent
Zhang et al.

(10) Patent No.: US 12,708,461 B2
(45) Date of Patent: Aug. 18, 2026

(54) SYSTEMS AND METHODS FOR ROBOTIC BRONCHOSCOPY

(71) Applicant: Noah Medical Corporation, Redwood City, CA (US)

(72) Inventors: Jian Zhang, San Mateo, CA (US); Carol Kayee Hung, Palo Alto, CA (US); Michael J. Shawver, Mill Valley, CA (US); Piotr Robert Slawinski, South San Francisco, CA (US); Kyle Ross Danna, Scotts Valley, CA (US); Hendrik Thompson, San Francisco, CA (US); Liya K. Abraha, San Francisco, CA (US); Kyle Robert Breton, Santa Cruz, CA (US)

(73) Assignee: Noah Medical Corporation, San Carlos, CA (US)

( * ) Notice: Subject to any disclaimer, the term of this patent is extended or adjusted under 35 U.S.C. 154(b) by 518 days.

(21) Appl. No.: 17/838,796

(22) Filed: Jun. 13, 2022

(65) Prior Publication Data

US 2022/0313375 A1 Oct. 6, 2022

Related U.S. Application Data

(63) Continuation of application No. PCT/US2020/065999, filed on Dec. 18, 2020.

(Continued)

(51) Int. Cl.

*A61B 34/30* (2016.01)
*A61B 1/00* (2006.01)

(Continued)

(52) U.S. Cl.

CPC .......... *A61B 34/30* (2016.02); *A61B 1/00103* (2013.01); *A61B 1/00149* (2013.01);

(Continued)

(58) Field of Classification Search

CPC ...... A61B 1/00149; A61B 1/01; A61B 1/2676

(Continued)

(56) References Cited

U.S. PATENT DOCUMENTS 6,397,907 B1 6/2002 Heintz
6,800,056 B2 10/2004 Tartaglia et al.

(Continued)

FOREIGN PATENT DOCUMENTS

CN 106175892 A 12/2016
CN 107427327 A 12/2017

(Continued)

OTHER PUBLICATIONS

Jaeger et al. Automated catheter navigation with electromagnetic image guidance. IEEE Transactions on Biomedical Engineering (2017).

(Continued)

*Primary Examiner* — Ryan N Henderson
*Assistant Examiner* — Pamela F Wu
(74) *Attorney, Agent, or Firm* — Wilson Sonsini Goodrich & Rosati

(57) ABSTRACT

An endoscopic robotic arm system and apparatus is provided. The devices and systems comprise various features improving the cost efficiency and reducing the complexity of manufacturing as well as usage. Disposable elongate members are described herein. The user interface device may also be adapted to the user behavior and may be personalized.

19 Claims, 37 Drawing Sheets

Related U.S. Application Data

(60) Provisional application No. 62/950,740, filed on Dec. 19, 2019.

(51) Int. Cl.
*A61B 1/01* (2006.01)
*A61B 1/267* (2006.01)
*A61B 90/00* (2016.01)
*A61B 90/30* (2016.01)
*A61B 17/00* (2006.01)
*A61B 34/00* (2016.01)
*A61B 34/20* (2016.01)

(52) U.S. Cl.
CPC .............. *A61B 1/01* (2013.01); *A61B 1/2676* (2013.01); *A61B 90/30* (2016.02); *A61B 90/361* (2016.02); *A61B 2017/00477* (2013.01); *A61B 2034/2059* (2016.02); *A61B 2034/258* (2016.02); *A61B 2034/301* (2016.02); *A61B 2090/365* (2016.02)

(58) Field of Classification Search
USPC ......................... 600/117, 121, 146, 150, 102
See application file for complete search history.

(56) References Cited

U.S. PATENT DOCUMENTS

| | | | | |
|---|---|---|---|---|
| 6,984,203 | B2 | 1/2006 | Tartaglia et al. | |
| 7,090,683 | B2 | 8/2006 | Brock et al. | |
| 7,775,972 | B2 | 8/2010 | Brock et al. | |
| 7,905,828 | B2 | 3/2011 | Brock et al. | |
| 7,922,650 | B2 | 4/2011 | McWeeney et al. | |
| 8,190,238 | B2 | 5/2012 | Moll et al. | |
| 8,439,830 | B2 | 5/2013 | Mckinley et al. | |
| 8,801,661 | B2 | 8/2014 | Moll et al. | |
| 8,961,533 | B2 | 2/2015 | Stahler et al. | |
| 9,066,740 | B2 | 6/2015 | Carlson et al. | |
| 9,414,738 | B2 | 8/2016 | Huszar et al. | |
| 9,457,168 | B2 | 10/2016 | Moll et al. | |
| 9,763,741 | B2 | 9/2017 | Alvarez et al. | |
| 10,130,427 | B2 | 11/2018 | Tanner et al. | |
| 10,136,959 | B2 | 11/2018 | Mintz et al. | |
| 10,299,870 | B2 | 5/2019 | Connolly et al. | |
| 10,426,559 | B2 | 10/2019 | Graetzel et al. | |
| 2004/0231206 | A1 | 11/2004 | Liebman et al. | |
| 2011/0213300 | A1 | 9/2011 | McWeeney et al. | |
| 2013/0090529 | A1 | 4/2013 | Boulais | |
| 2016/0184032 | A1* | 6/2016 | Romo | B25J 13/085 901/46 |
| 2016/0361128 | A1* | 12/2016 | Seeber | A61B 34/30 |
| 2018/0070935 | A1* | 3/2018 | Fenech | A61B 34/30 |
| 2018/0177383 | A1 | 6/2018 | Noonan et al. | |
| 2018/0184887 | A1 | 7/2018 | Abou El Kheir | |
| 2019/0053861 | A1 | 2/2019 | Lwin et al. | |
| 2019/0110843 | A1 | 4/2019 | Ummalaneni | |
| 2019/0206563 | A1 | 7/2019 | Shelton, IV et al. | |
| 2019/0269885 | A1 | 9/2019 | Bailey et al. | |
| 2019/0272917 | A1* | 9/2019 | Couture | A61B 34/25 |
| 2019/0365209 | A1 | 12/2019 | Ye et al. | |
| 2020/0315716 | A1* | 10/2020 | Penny | A61B 1/00128 |
| 2022/0008152 | A1* | 1/2022 | Rohr Daniel | A61B 34/25 |

FOREIGN PATENT DOCUMENTS

| | | | |
|---|---|---|---|
| JP | 2013519486 | A | 5/2013 |
| JP | 2017502709 | A | 1/2017 |
| JP | 2017532171 | A | 11/2017 |
| KR | 20190054030 | A | 5/2019 |
| WO | WO-2008018256 | A1 | 2/2008 |
| WO | WO-2018069992 | A1 | 4/2018 |
| WO | WO-2021127426 | A1 | 6/2021 |

OTHER PUBLICATIONS

Moataz et al. Three-dimensional angiography using mobile c-arm with IMU sensor attached: initial study. IEEE (2015).

PCT/US2020/065999 Search Report & Written Opinion dated Mar. 4, 2021.

EP20901776.3 Extended European Search Report dated Jan. 25, 2024.

* cited by examiner

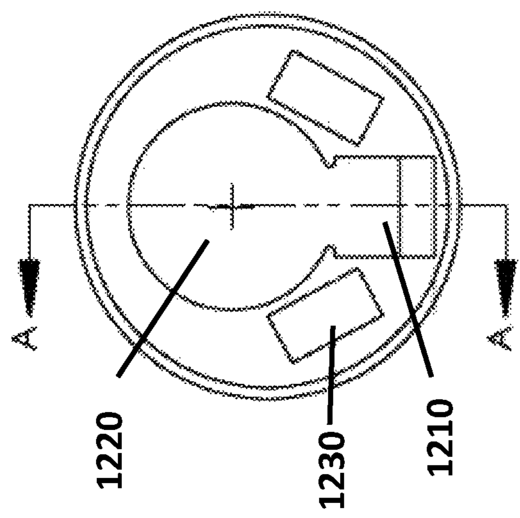
FIG. 12
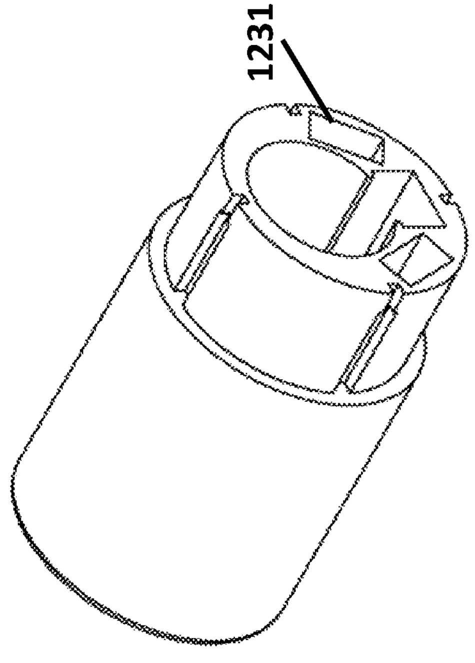

1415
1421
1410
1411
1413
1420
1423

1930
1920
Menu
Menu 1910
1911

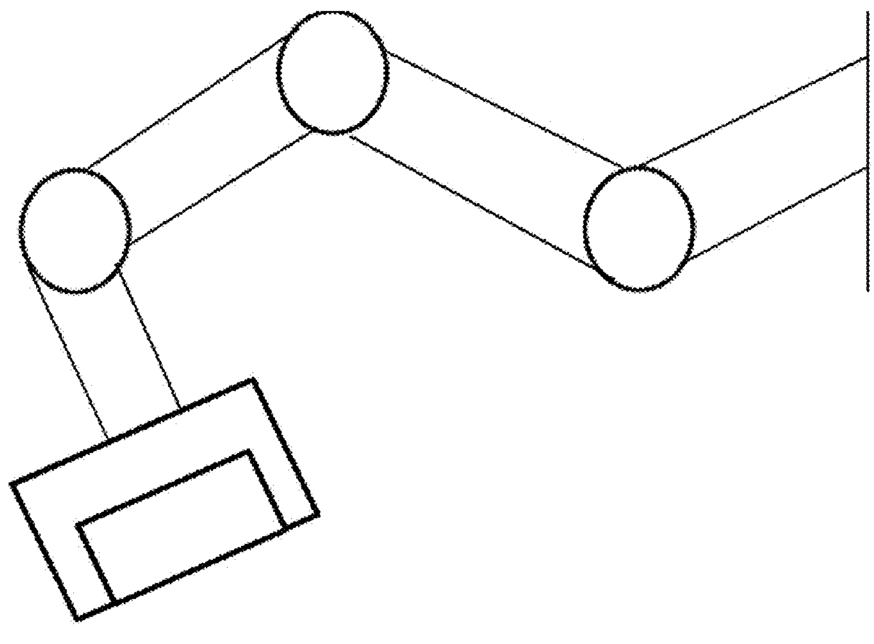
FIG. 22
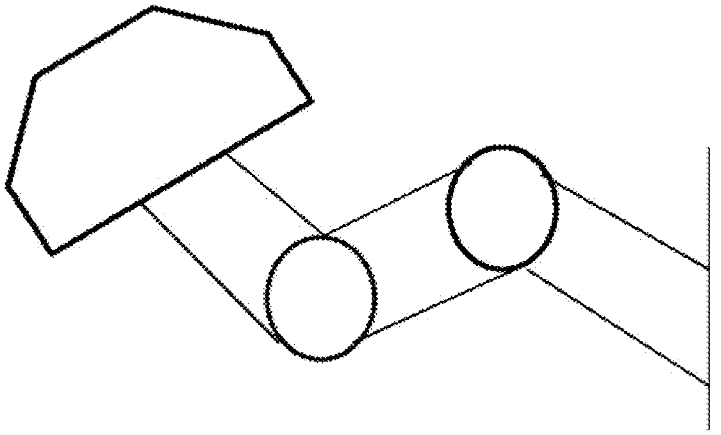

SYSTEMS AND METHODS FOR ROBOTIC BRONCHOSCOPY

REFERENCE

This application is a Continuation Application of International Application No. PCT/US2020/065999, filed Dec. 18, 2020, which claims priority to U.S. Provisional Patent Application No. 62/950,740, filed Dec. 19, 2019, each of which is entirely incorporated herein by reference.

BACKGROUND OF THE INVENTION

Early diagnosis of lung cancer is critical. The five-year survival rate of lung cancer is around 18% which is significantly lower than next three most prevalent cancers: breast (90%), colorectal (65%), and prostate (99%). A total of 142,000 deaths were recorded in 2018 due to lung cancer.

In general, a typical lung cancer diagnosis and surgical treatment process can vary drastically, depending on the techniques used by healthcare providers, the clinical protocols, and the clinical sites. The inconsistent process can delay the diagnosis of the cancer as well as imposing a high cost on the patient and the health care system.

SUMMARY OF THE INVENTION

Recognized herein is a need for a minimally invasive system that allows for performing surgical procedures or diagnostic operations with improved reliability and cost-efficiency. The present disclosure provides systems and methods allowing for standardized early lung cancer diagnosis and treatment at reduced cost. The present disclosure provides accessible, more cost-effective methods and systems for early stage diagnosis and treatment of cancers. In some embodiments of the invention, at least a portion of the robotic bronchoscopy system is disposable. For instance, the catheter portion may be designed to be disposable at low cost while preserving the surgical performance capability and functionality. Moreover, the provided robotic bronchoscopy system is designed with capability to access hard-to-reach tissues such as bronchus, lung, without introducing extra cost. It should be noted that the provided robotic systems can be used in various minimally invasive surgical procedures that involve various types of tissue including heart, bladder and lung tissue and others.

According to some aspects of the disclosure, a robotic endoscopic apparatus is provided. The apparatus may include a disposable elongate member comprising a proximal end and a distal end and the proximal end is removably attached to a robotic arm. The distal end comprises a plurality of pull wires and the pull wires integrated with the walls of the elongate member. The elongate member may also be referred to as bronchoscope, catheter which can be used interchangeably throughout the specification.

In an aspect, a robotic endoscopic apparatus is provided. The robotic endoscopic apparatus comprises: a disposable elongate member comprising: a proximal end and a distal end, wherein the proximal end is removably attached to a robotic arm via a handle, wherein the distal end is integrated with an imaging device, a position sensor and an illumination device; and a bending section that is articulated by one or more pull wires.

In some embodiments, the distal end comprises a structure to receive the imaging device, the position sensor, and the illumination device. In some embodiments, the imaging device, the position sensor, and the illumination device are arranged into a compact configuration. In some embodiments, the handle includes one or more components configured to process image data, provide power to the imaging device, the position sensor and the illumination device, or establish communication with an external device.

In some embodiments, the handle comprises an interface configured to couple the handle to an instrument driving mechanism attached to the robotic arm. In some cases, the interface includes an electrical interface and a mechanical interface. In some instances, the mechanical interface is configured to releasably couple the handle to the instrument driving mechanism. In some cases, the apparatus further comprises an anti-buckling mechanism with an alignment feature. For example, the alignment feature is configured to assist an alignment between the instrument driving mechanism and the anti-buckling mechanism. In some examples, the alignment feature includes a magnetic component, a laser or a click button. In some examples, the anti-buckling mechanism comprises a series of connected cylinders each including a lip structure. In some instances, the lip structure of each cylinder has a hold with same diameter.

In some embodiments, a robotic endoscopic system comprising the robotic endoscopic apparatus and a user interface device configured for a user to control a movement of the robotic endoscopic apparatus. In some cases, the user interface device is personalized based on past user behavior. In some instances, the user interface device is personalized with aid of a machine learning algorithm trained model. In some cases, the robotic endoscopic system further comprises a display configured to display image data captured by the imaging device overlaid with virtual renderings of one or more components. In some instances, the display of the virtual renderings of the one or more components is selectively enabled or disabled by a user.

In some embodiments, both the handle and the disposable elongate member are single-use. In some embodiments, the one or more pull wires are individually attached to the bending section according to a selected configuration pattern. In some embodiments, a control of the articulation of the robotic endoscopic apparatus is based at least in part on a virtual mapping algorithm. In some cases, the virtual mapping algorithm maps the selected configuration pattern to an updated configuration pattern upon a change of state of the one or more pull wires.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12 shows an example distal portion of a catheter with integrated imaging device and illumination device.

FIG. 22 shows an example portable robotic cone beam CT.

DETAILED DESCRIPTION OF THE INVENTION

Figure 1:
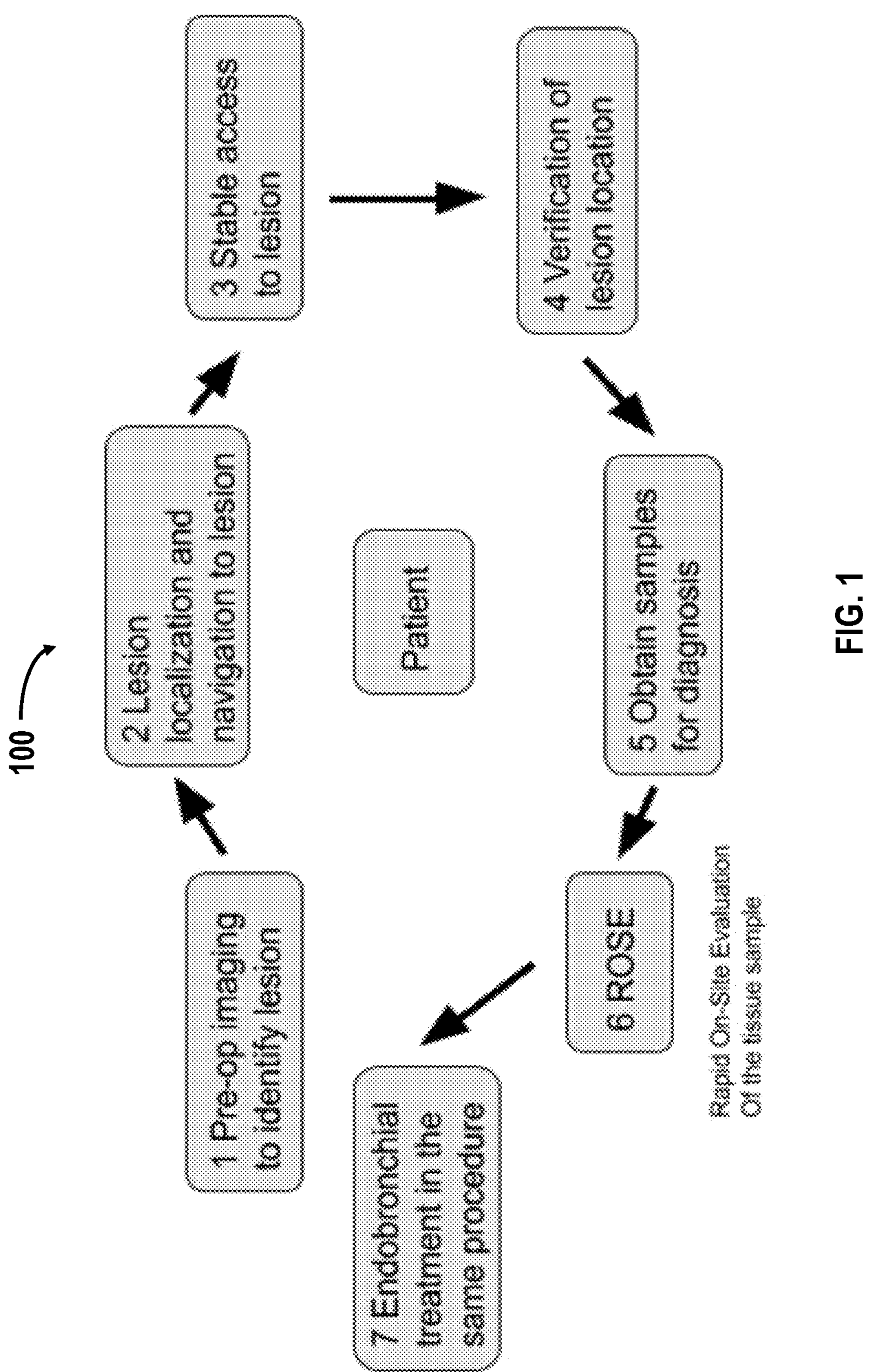
FIG. 1 shows an example workflow of standardized lung cancer diagnosis enabled by the robotic bronchoscopy system described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

While exemplary embodiments will be primarily directed at a bronchoscope, one of skill in the art will appreciate that this is not intended to be limiting, and the devices described herein may be used for other therapeutic or diagnostic procedures and in other anatomical regions of a patient's body such as a digestive system, including but not limited to the esophagus, liver, stomach, colon, urinary tract, or a respiratory system, including but not limited to the bronchus, the lung, and various others.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of diagnosis or surgical procedures as described herein are presented in the context of pulmonary diagnosis or surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU) or a microcontroller), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

As used herein, the terms distal and proximal may generally refer to locations referenced from the apparatus, and can be opposite of anatomical references. For example, a distal location of a bronchoscope or catheter may correspond to a proximal location of an elongate member of the patient, and a proximal location of the bronchoscope or catheter may correspond to a distal location of the elongate member of the patient.

A system as described herein, includes an elongate portion or elongate member such as a catheter. The terms "elongate member", "catheter", "bronchoscope" are used interchangeably throughout the specification unless contexts suggest otherwise. The elongate member can be placed directly into the body lumen or a body cavity. In some embodiments, the system may further include a support apparatus such as a robotic manipulator (e.g., robotic arm) to drive, support, position or control the movements and/or operation of the elongate member. Alternatively or in addition to, the support apparatus may be a hand-held device or other control devices that may or may not include a robotic system. In some embodiments, the system may further include peripheral devices and subsystems such as imaging systems that would assist and/or facilitate the navigation of the elongate member to the target site in the body of a subject.

In some embodiments of the present disclosure, a robotic bronchoscopy system is provided for performing surgical operations or diagnosis with improved performance at low cost. For example, the robotic bronchoscopy system may comprise a steerable catheter that can be entirely disposable. This may beneficially reduce the requirement of sterilization which can be high in cost or difficult to operate, yet the sterilization or sanitization may not be effective. Moreover, one challenge in bronchoscopy is reaching the upper lobe of the lung while navigating through the airways. In some cases, the provided robotic bronchoscopy system may be designed with capability to navigate through the airway having a small bending curvature in an autonomous or semi-autonomous manner. Alternatively, the robotic bronchoscopy system may be navigated by an operator through a control system with vision guidance.

A typical lung cancer diagnosis and surgical treatment process can vary drastically, depending on the techniques used by healthcare providers, the clinical protocols, and the clinical sites. The inconsistent processes may cause delay to diagnose lung cancers in early stage, high cost of healthcare system and the patients to diagnose and treat lung cancers, and high risk of clinical and procedural complications. The provided robotic bronchoscopy system may allow for standardized early lung cancer diagnosis and treatment. FIG. 1 shows an example workflow 100 of standardized lung cancer diagnosis enabled by the robotic bronchoscopy system described herein.

As illustrated in FIG. 1, pre-operative imaging may be performed to identify lesions. Any suitable imaging modalities such as magnetic resonance (MR), positron emission tomography (PET), X-ray, computed tomography (CT) and ultrasound may be used to identify lesions or regions of interest. For instance, a patient with suspect lung cancer may be administered a pre-operative CT scan and suspect lung nodules may be identified in the CT images. The pre-operative imaging process can be performed prior to the bronchoscopy.

Next, the CT images may be analyzed to generate a map to guide the navigation of the robotic bronchoscope at the time of bronchoscopy. For example, the lesion or the region of interest (ROI) may be segmented on the images. When the lung is under imaging, the passage or pathway to the lesion may be highlighted on the reconstructed images for planning a navigation path. The reconstructed images may guide the navigation of the robotic bronchoscope to the target tissue or target site. In some cases, the navigation path may be pre-planned using 3D image data. For instance, the catheter may be advanced toward the target site under a robotic control of the robotic bronchoscope system. The catheter may be steered or advanced towards the target site in a manual manner, an autonomous manner, or a semi-autonomous manner. In an example, the movement of the catheter may be image guided such that the insertion and/or steering direction may be controlled automatically.

In some cases, the lesion location in the pre-operative imaging may not be accurate due to patient motion or body divergence. In such cases, the lesion location may be verified prior to a surgical procedure (e.g., biopsy or treatment). The accurate location of the lesion may be verified or updated with aid of the robotic bronchoscopy system. For instance, the bronchoscopy system may provide interface to imaging modalities such as fluoroscopy to provide in vivo real-time imaging of the target site and the surrounding areas to locate the lesion. In an example, a C arm or O arm fluoroscopic imaging system may be used to generate a tomosynthesis image for verifying or updating the location of the lesion. Proceeding to the surgical procedures such as biopsy, various surgical tools such as biopsy tools, brushes or forceps may be inserted into the working channel of the catheter to perform biopsy or other surgical procedures manually or automatically.

Next, samples of the lesion or any other target tissue may be obtained by the tools inserted through the working channel of the catheter. The system allows for camera visualization to be maintained throughout the procedure, including during the insertion of tools through the working channel. In some cases, the tissue sample may be rapidly evaluated on-site by a rapid on-site evaluation process to determine whether repetition of the tissue sampling is needed, or to decide further action. In some cases, the rapid on-site evaluation process may also provide a quick analysis on the tissue sample to determine the following surgical treatment. For instance, if the tissue sample is determined to be malignant as a result of the rapid on-site evaluation process, a manual or robotic treatment instrument may be inserted through the working channel of the robotic bronchoscope and perform endobronchial treatment of the lung cancer. This beneficially allows for diagnosis and treatment being performed in one session thereby providing targeted, painless, and fast treatment of early stage lung cancer.

Figure 2A:
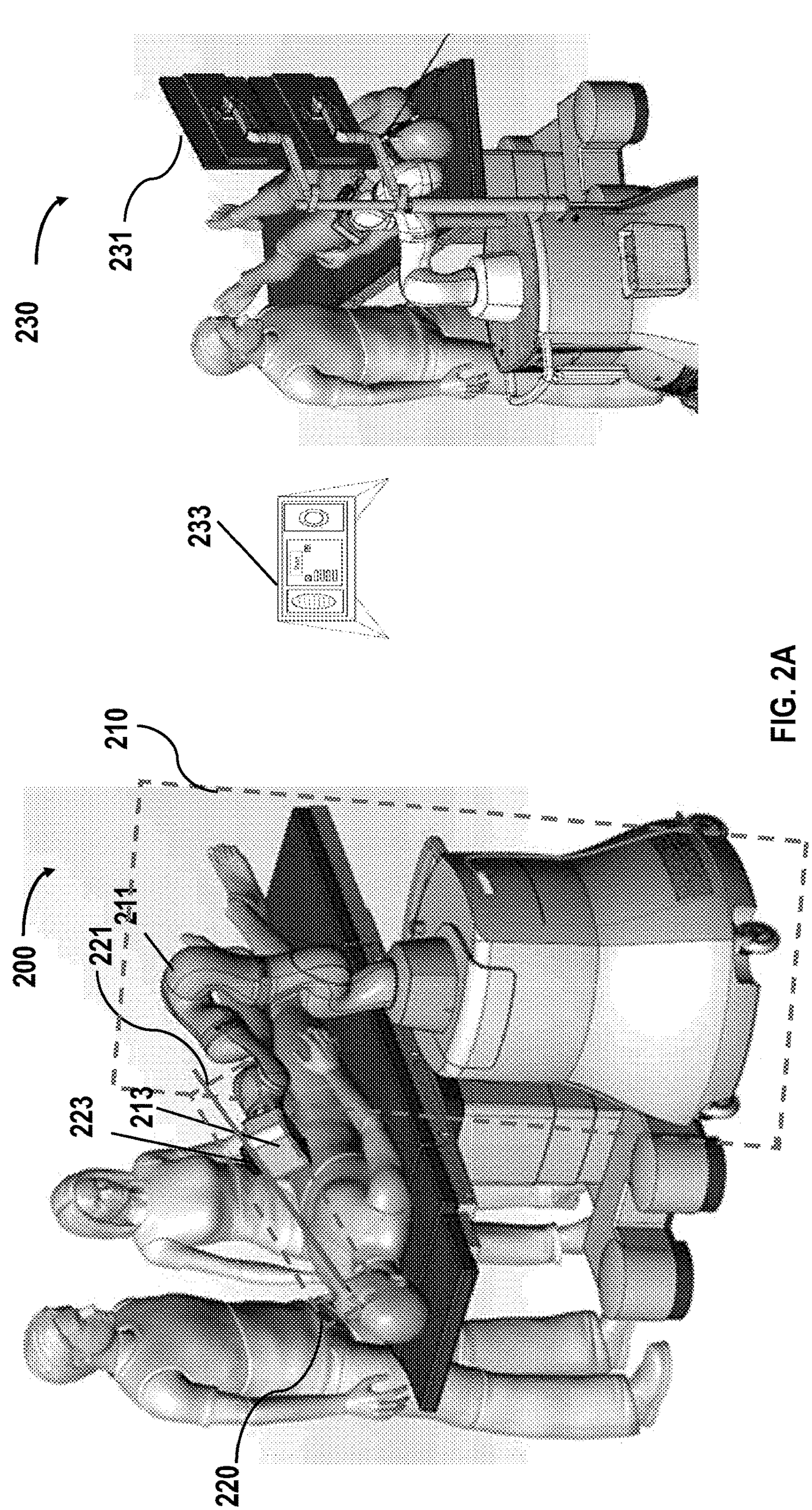
FIG. 2A shows examples of robotic bronchoscopy systems, in accordance with some embodiments of the invention.
Figure 2B:
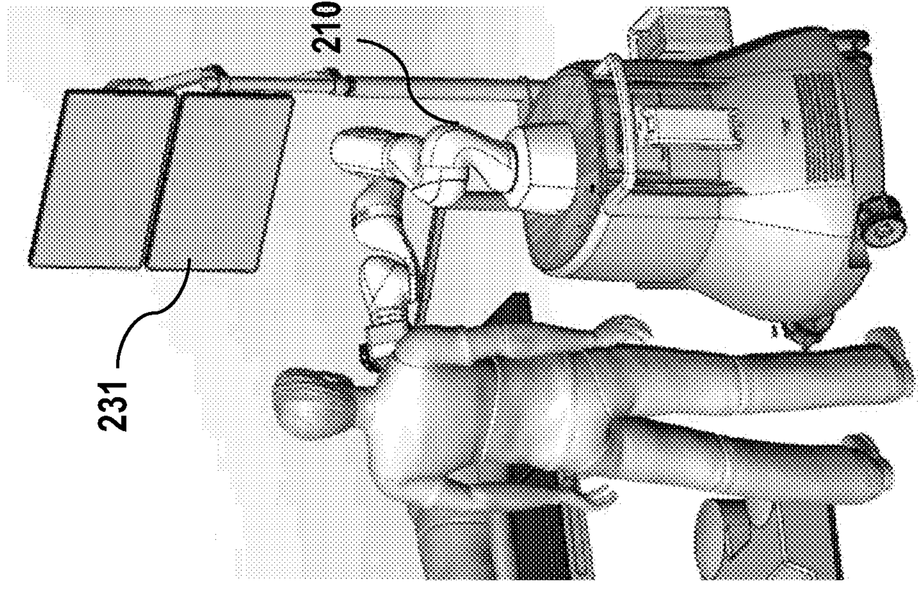
FIG. 2B shows different views of an example robotic bronchoscopy system, in accordance with some embodiments of the invention.

FIGS. 2A and 2B show examples of robotic bronchoscopy system 200, 230, in accordance with some embodiments of the invention. As shown in FIG. 2A, the robotic bronchoscopy system 200 may comprise a steerable catheter assembly 220 and a robotic support system 210, for supporting or carrying the steerable catheter assembly. The steerable catheter assembly can be a bronchoscope. In some embodiments, the steerable catheter assembly may be a single-use robotic bronchoscope. In some embodiments, the robotic bronchoscopy system 200 may comprise an instrument driving mechanism 213 that is attached to the arm of the robotic support system. The instrument driving mechanism may be provided by any suitable controller device (e.g., hand-held controller) that may or may not include a robotic system. The instrument driving mechanism may provide mechanical and electrical interface to the steerable catheter assembly 220. The mechanical interface may allow the steerable catheter assembly 220 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

The steerable catheter assembly 220 may comprise a handle portion 223 that may include components configured to processing image data, provide power, or establish communication with other external devices. For instance, the handle portion 223 may include a circuitry and communication elements that enables electrical communication between the steerable catheter assembly 220 and the instrument driving mechanism 213, and any other external system or devices. In another example, the handle portion 223 may comprise circuitry elements such as power sources for powering the electronics (e.g. camera and LED lights) of the endoscope. In some cases, the handle portion may be in electrical communication with the instrument driving mechanism 213 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 213 may provide a mechanical interface only. The handle portion may be in electrical communication with a modular wireless communication device or any other user device (e.g., portable/hand-held device or controller) for transmitting sensor data and/or receiving control signals. Details about the handle portion are described later herein.

The steerable catheter assembly 220 may comprise a flexible elongate member 211 that is coupled to the handle portion. In some embodiments, the flexible elongate member may comprise a shaft, steerable tip and a steerable section. The steerable catheter assembly may be a single use robotic bronchoscope. In some cases, only the elongate member may be disposable. In some cases, at least a portion of the elongate member (e.g., shaft, steerable tip, etc) may be disposable. In some cases, the entire steerable catheter assembly 220 including the handle portion and the elongate member can be disposable. The flexible elongate member and the handle portion are designed such that the entire steerable catheter assembly can be disposed of at low cost. Details about the flexible elongate member and the steerable catheter assembly are described later herein.

In some embodiments, the provided bronchoscope system may also comprise a user interface. As illustrated in the example system 230, the bronchoscope system may include a treatment interface module 231 (user console side) and/or a treatment control module 233 (patient and robot side). The treatment interface module may allow an operator or user to interact with the bronchoscope during surgical procedures. In some embodiments, the treatment control module 233 may be a hand-held controller. The treatment control module may, in some cases, comprise a proprietary user input device and one or more add-on elements removably coupled to an existing user device to improve user input experience. For instance, physical trackball or roller can replace or supplement the function of at least one of the virtual graphical element (e.g., navigational arrow displayed on touchpad) displayed on a graphical user interface (GUI) by giving it similar functionality to the graphical element which it replaces. Examples of user devices may include, but are not limited to, mobile devices, smartphones/cellphones, tablets, personal digital assistants (PDAs), laptop or notebook computers, desktop computers, media content players, and the like. Details about the user interface device and user console are described later herein.

FIG. 2B shows different views of a bronchoscope system. The user console 231 may be mounted to the robotic support system 210. Alternatively or in addition to, the user console or a portion of the user console (e.g., treatment interface module) may be mounted to a separate mobile cart.

Robotic Endoluminal Platform

In one aspect, a robotic endoluminal platform is provided. In some cases, the robotic endoluminal platform may be a bronchoscopy platform. The platform may be configured to perform one or more operations consistent with the method described in FIG. 1. FIGS. 3-7 show various examples of a robotic endoluminal platform and its components or subsystems, in accordance with some embodiments of the invention. In some embodiments, the platform may comprise a robotic bronchoscopy system and one or more subsystems that can be used in combination with the robotic bronchoscopy system of the present disclosure.

Figure 3A:
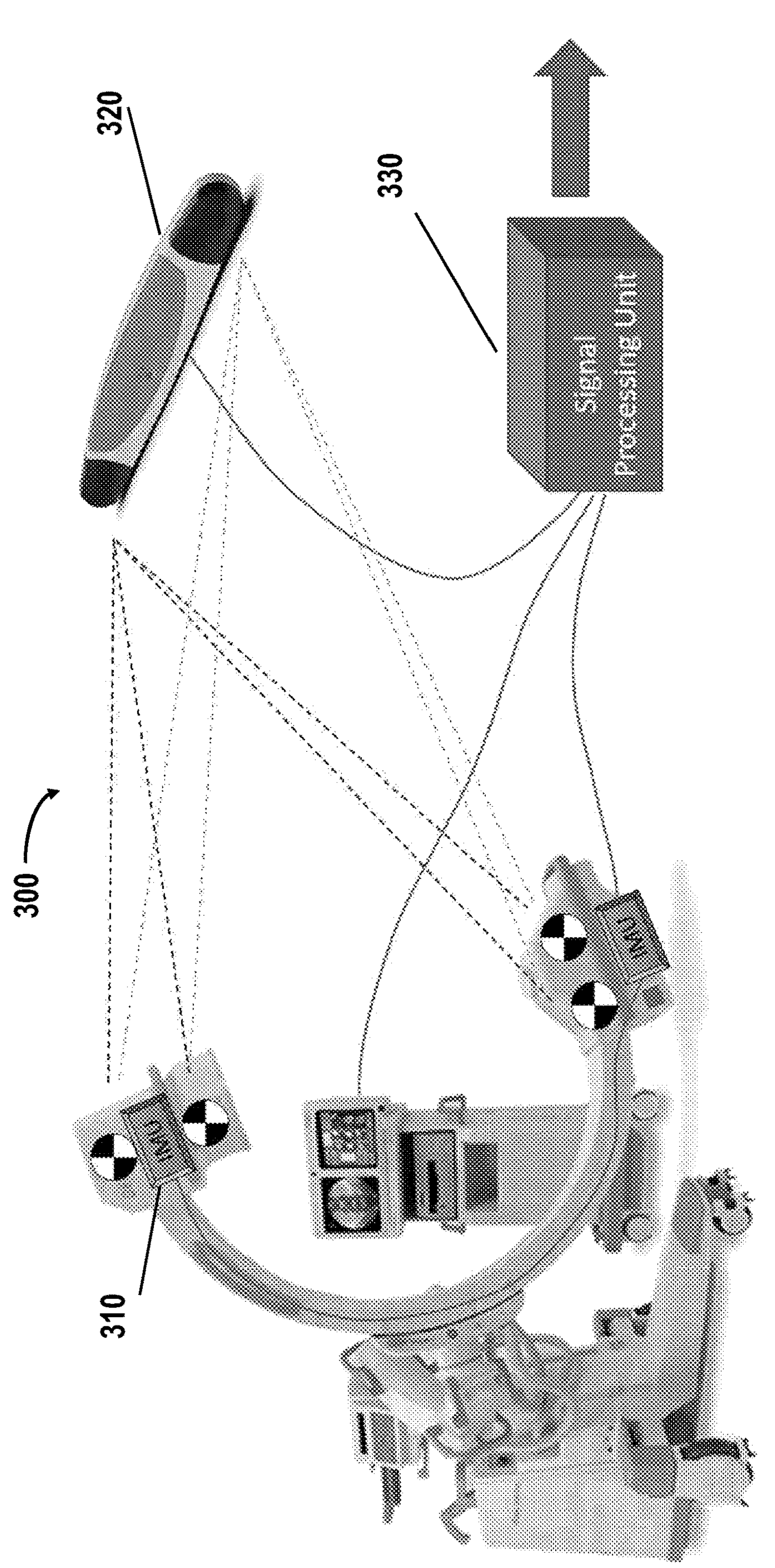
FIG. 3A shows an example of a fluoroscopy (tomosynthesis) imaging system.
Figure 3B:
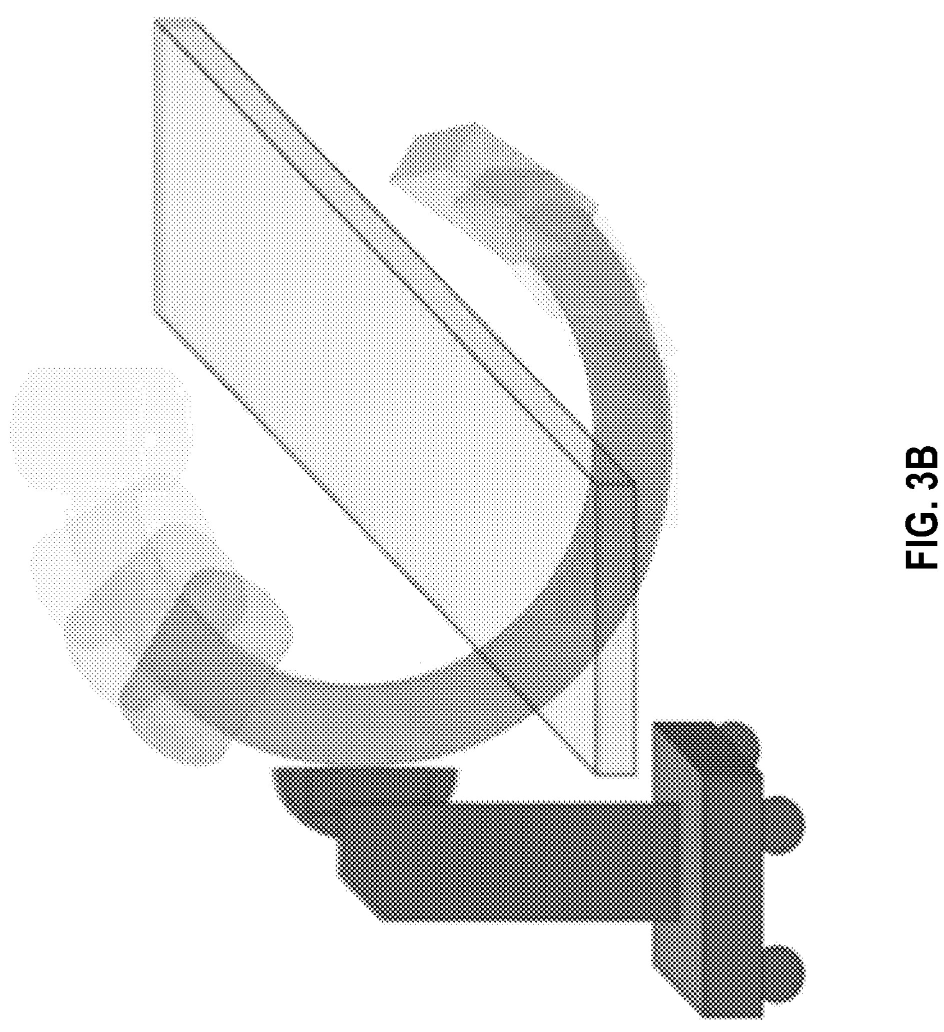
FIG. 3B shows a C-arm fluoroscopy (tomosynthesis) imaging system in different (rotation) poses while taking images of a subject.

In some embodiments, the one or more subsystems may include imaging systems such as a fluoroscopy (tomosynthesis) imaging system for providing real-time imaging of a target site (e.g., comprising lesion). FIG. 3A shows an example of a fluoroscopy (tomosynthesis) imaging system 300. For example, the fluoroscopy (tomosynthesis) imaging system may perform accurate lesion location tracking or verification before or during surgical procedure as described in FIG. 1. In some cases, lesion location may be tracked based on location data about the fluoroscopy (tomosynthesis) imaging system/station (e.g., C arm) and image data captured by the fluoroscopy (tomosynthesis) imaging system. The lesion location may be registered with the coordinate frame of the robotic bronchoscopy system. The location or motion of the fluoroscopy (tomosynthesis) imaging system may be measured using any suitable motion/location sensors 310 such as inertial measurement units (IMUs)), one or more gyroscopes, velocity sensors, accelerometers, magnetometers, location sensors (e.g., global positioning system (GPS) sensors), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses) and/or field sensors (e.g., magnetometers, electromagnetic sensors, radio sensors). The one or more sensors for tracking the motion and location of the fluoroscopy (tomosynthesis) imaging station may be disposed on the imaging station or be located remotely from the imaging station, such as a wall-mounted camera 320. FIG. 3B shows a C-arm fluoroscopy (tomosynthesis) imaging system in different (rotation) poses while taking images of a subject. The various poses may be captured by the one or more sensors as described above.

In some embodiments, a location of lesion may be segmented in the image data captured by the fluoroscopy (tomosynthesis) imaging system with aid of a signal processing unit 330. One or more processors of the signal processing unit may be configured to further overlay treatment locations (e.g., lesion) on the real-time fluoroscopic image/video. For example, the processing unit may be configured to generate an augmented layer comprising augmented information such as the location of the treatment location or target site. In some cases, the augmented layer may also comprise graphical marker indicating a path to this target site. The augmented layer may be a substantially transparent image layer comprising one or more graphical elements (e.g., box, arrow, etc). The augmented layer may be superposed onto the optical view of the optical images or video stream captured by the fluoroscopy (tomosynthesis) imaging system, and/or displayed on the display device. The transparency of the augmented layer allows the optical image to be viewed by a user with graphical elements overlay on top of. In some cases, both the segmented lesion images and an optimum path for navigation of the elongate member to reach the lesion may be overlaid onto the real time tomosynthesis images. This may allow operators or users to visualize the accurate location of the lesion as well as a planned path of the bronchoscope movement. In some cases, the segmented and reconstructed images (e.g. CT images as described elsewhere) provided prior to the operation of the systems described herein may be overlaid on the real time images.

In some embodiments, the one or more subsystems of the platform may comprise a navigation and localization subsystem. The navigation and localization subsystem may be configured to construct a virtual airway model based on the pre-operative image (e.g., pre-op CT image). The navigation and localization subsystem may be configured to identify the segmented lesion location in the 3D rendered airway model and based on the location of the lesion, the navigation and localization subsystem may generate an optimal path from the main bronchi to the lesions with a recommended approaching angle towards the lesion for performing surgical procedures (e.g., biopsy).

At a registration step before driving the bronchoscope to the target site, the system may align the rendered virtual view of the airways to the patient airways. Image registration may consist of a single registration step or a combination of a single registration step and real-time sensory updates to registration information. Once registered, all airways may be aligned to the pre-operative rendered airways. During robotic bronchoscope driving towards the target site, the location of the bronchoscope inside the airways may be tracked and displayed. In some cases, location of the bronchoscope with respect to the airways may be tracked using positioning sensors. Other types of sensors (e.g. camera) can also be used instead of or in conjunction with the positioning sensors using sensor fusion techniques. Positioning sensors such as electromagnetic (EM) sensors may be embedded at the distal tip of the catheter and an EM field generator may be positioned next to the patient torso during procedure. The EM field generator may locate the EM sensor position in 3D space or may locate the EM sensor position and orientation in 5D or 6D space. This may provide a visual guide to an operator when driving the bronchoscope towards the target site.

Figure 4A:
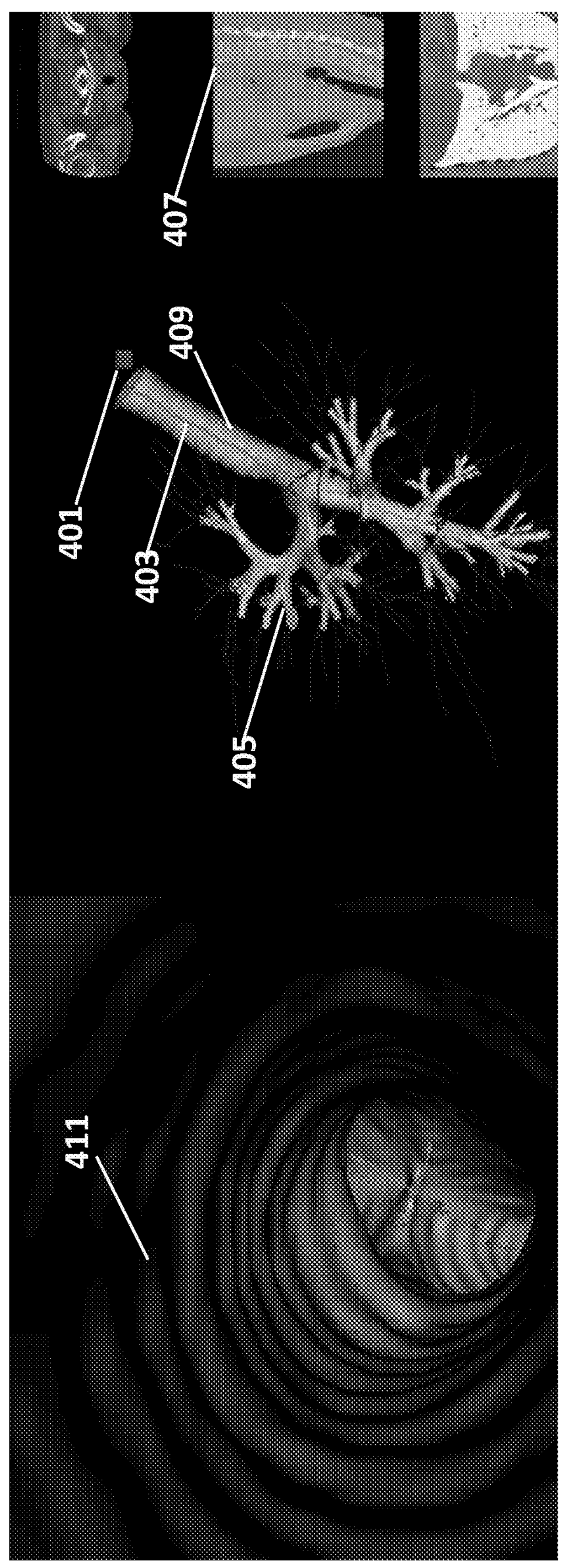
FIG. 4A shows an example of a user interface for visualizing a virtual airway overlaid with an optimal path, location of the tip of the catheter, and lesion location.

FIG. 4A shows an example of a user interface for visualizing a virtual airway 409 overlaid with an optimal path 403, location of the tip of the catheter 401, and lesion location 405. In this example, the location of the tip of the catheter is displayed in real-time relative to the virtual airway model 409 thereby providing visual guidance. As shown in the example of FIG. 4A, during robotic bronchoscope driving, the optimal path 403 may be displayed and overlaid onto the virtual airway model. As described above, the virtual airway model may be constructed based on the real-time fluoroscopic image/video (and location data of the imaging system). In some cases, a view of the real-time fluoroscopic image/video 407 may also be displayed on the graphical user interface. In some cases, users may also be permitted to access the camera view or image/video 411 captured by the bronchoscope in real time.

In some embodiments, the user interface may further include a user device allowing a user to visualize virtual renderings (e.g., airways) and live camera views when the devices is navigated to targets during the procedure. In some cases, the virtual renderings may be overlaid onto the live camera view and displayed on a display device. In some cases, the system may be integrated with or utilize immersive technologies such as immersive, virtual reality (VR) and augmented reality (AR) enabled systems to enable visualization of the virtual renderings.

For example, user may be permitted to visualize the overlays (e.g., pathway, target, vasculature, other anatomical structures) on these views with or without augmented reality systems thereby providing the user information during the procedure. The system may also permit users to select/control display of the overlays based on use cases or user preferences.

Figure 4B:
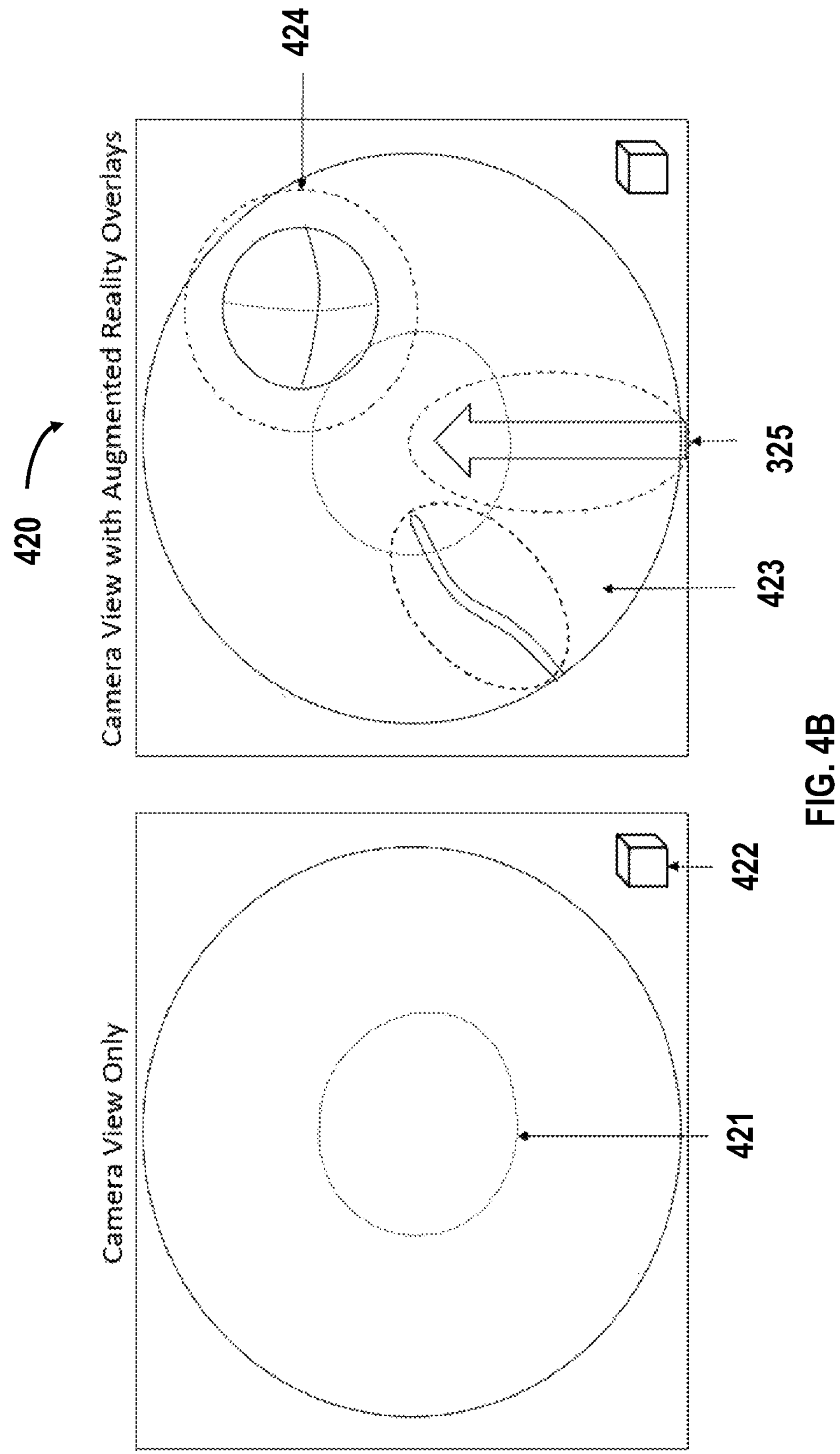
FIG. 4B shows examples of navigation views with augmented information.

FIG. 4B shows examples of navigation views with the augmented information. As shown in FIG. 4B, the navigation view 420 may include at least a live camera view 421 overlaid with virtual renderings, e.g., augmented reality information. The virtual renderings or overlaid information may include a plurality of components such as a virtual airway 423, a virtual lesion 424, a virtual panned path to the lesion 425 and the like. The plurality of virtual components may be visualized with or without use of virtual/augmented reality device. The navigation view may also include a directional indicator 424 indicating navigation directions (e.g., anterior, superior, inferior, posterior, left, right).

Figure 4C:
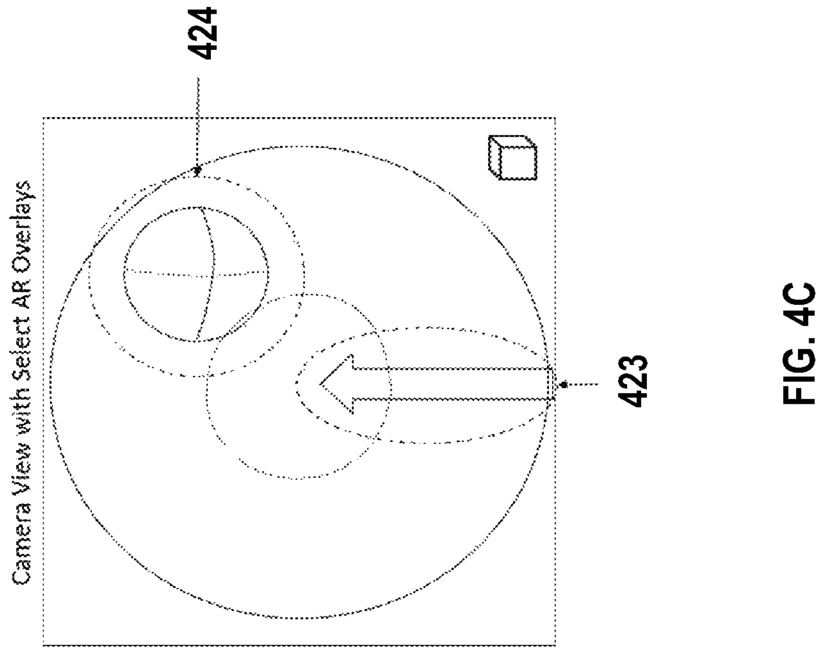
FIG. 4C shows an example of a navigation view with user selected virtual renderings.
Figure 4D:
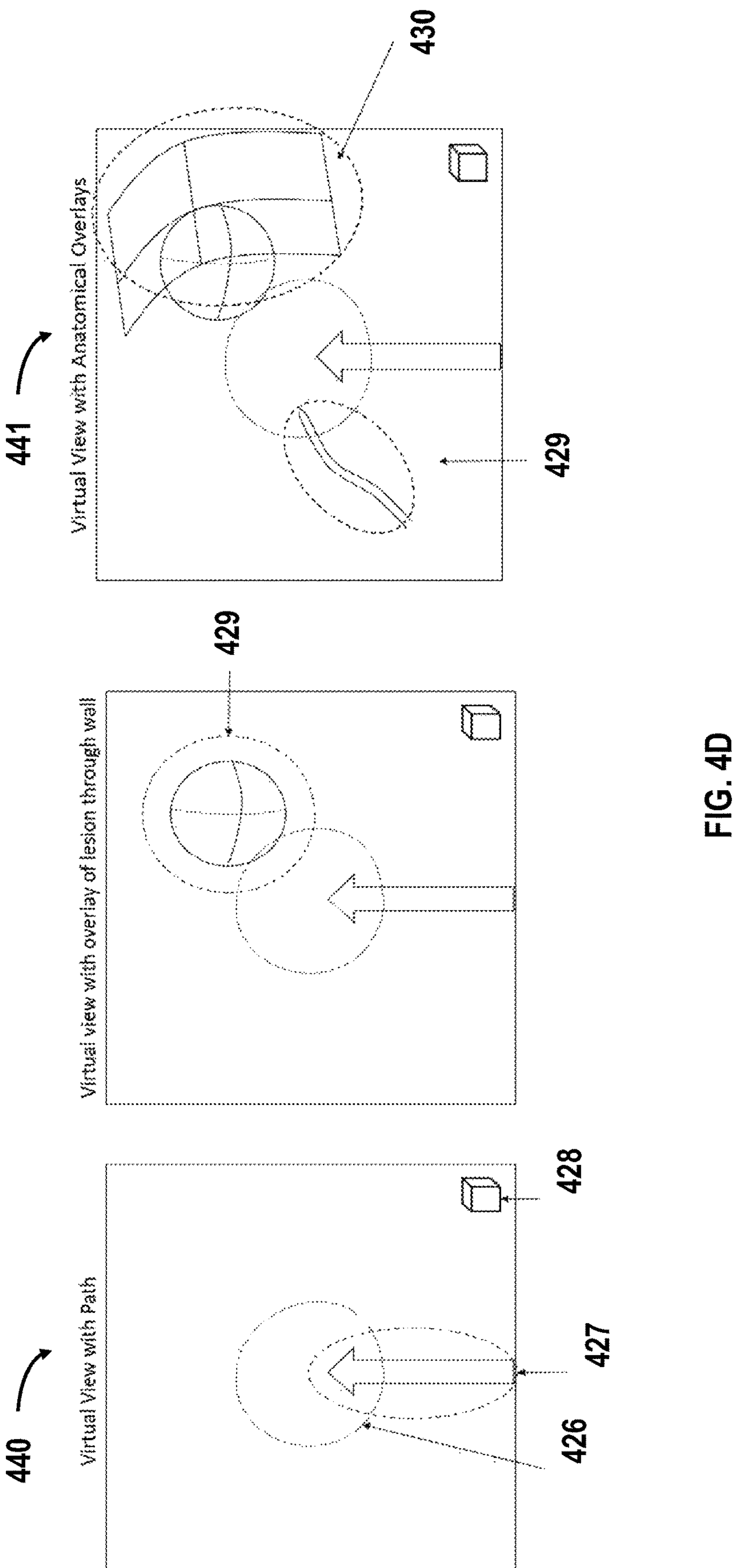
FIG. 4D shows examples of endoluminal views.

The provided system may beneficially allow users to control the display of the virtual renderings based on user preference. For example, a user may enable/disable the display of one or more components selected from the plurality of components. FIG. 4C shows an example of a navigation view with user selected virtual renderings. For instance, a user may toggle off the virtual renderings of the airway and view a live camera view overlaid with the selected virtual rendering of lesion 424 and path 423. FIG. 4D shows examples of endoluminal views. In the example 440, a virtual lumen 426 may be displayed along with virtual rendering of the planned path 427 and/or vasculature 429. Similarly, a user may be provided with a directional indicator 428 within the view. In another example 441, a user may turn on the virtual rendering of an airway 429 and pleural 430 such that these virtual components are overlaid onto the lumen view. A user can switch on/off of any selected components at any time.

In some embodiments, the one or more subsystems of the platform may comprise one or more treatment subsystems such as manual or robotic instruments (e.g., biopsy needles, biopsy forceps, biopsy brushes) and/or manual or robotic therapeutical instruments (e.g., RF ablation instrument, Cryo instrument, Microwave instrument, and the like).

Figure 5:
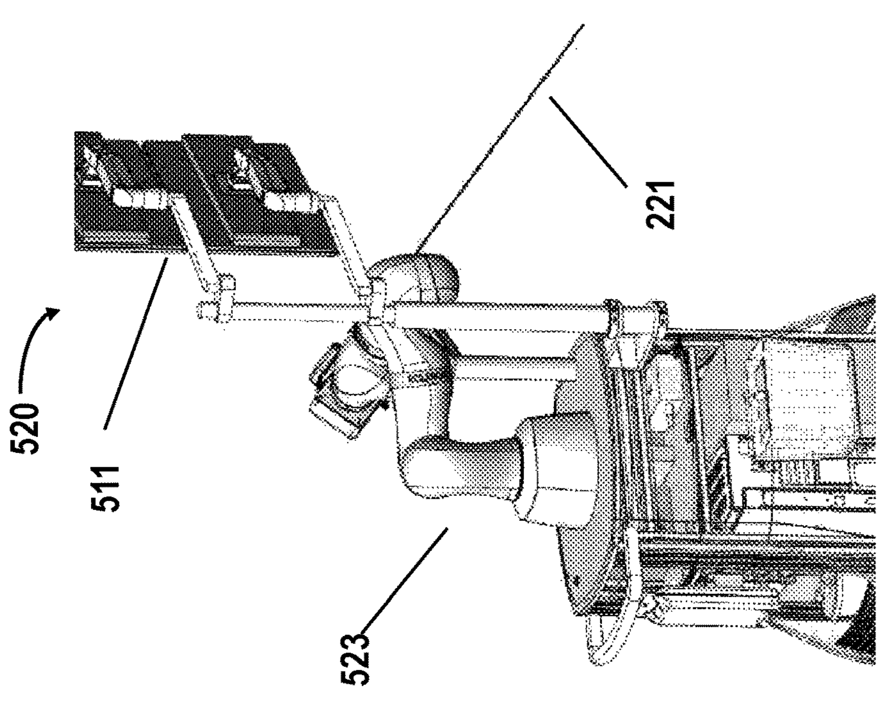
FIG. 5 shows an example treatment interface module allowing an operator or user to interact with the bronchoscope during surgical procedures.
Figure 5:
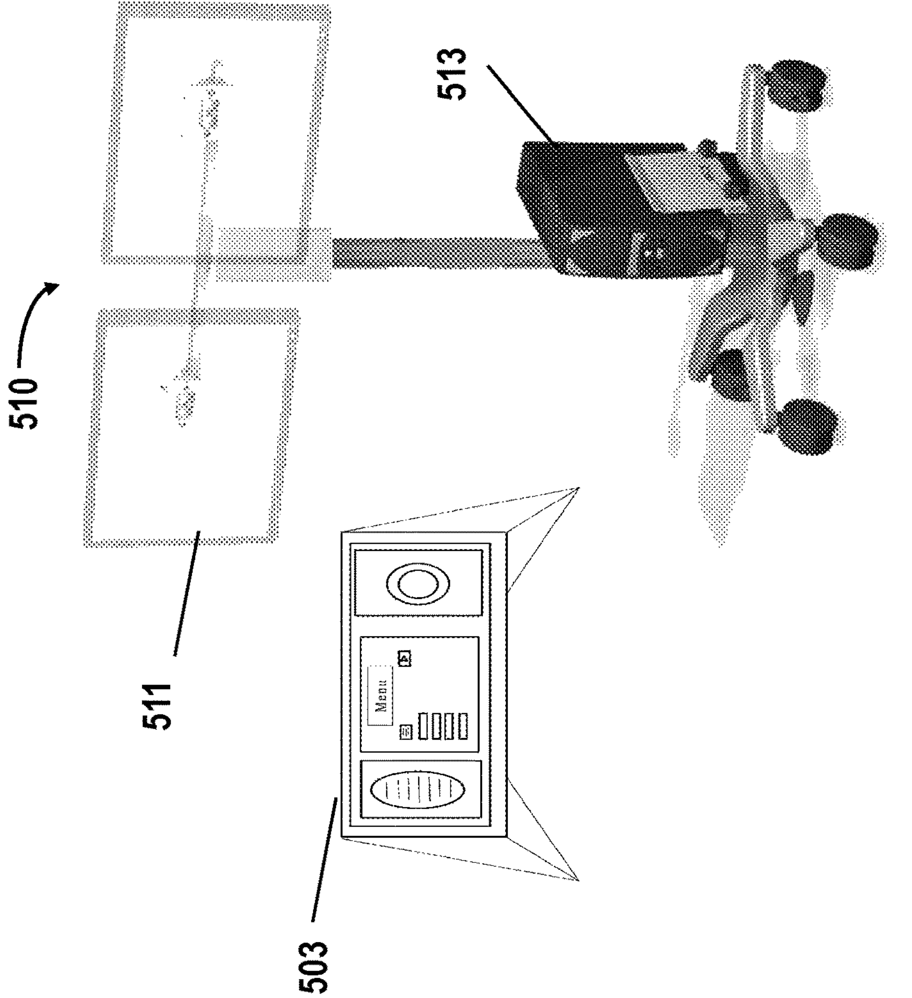

In some embodiments, the one or more subsystems of the platform may comprise a user console including a treatment interface module (user console side) and/or a treatment control module (patient and robot side). FIG. 5 shows an example of a user console allowing an operator or user to interact with the bronchoscope during surgical procedures. As shown in the example 510, the user console may comprise a treatment interface module configured to provide a user interface 511 displaying information related to using of the bronchoscope such as navigation information, user information (e.g., control parameters), robotic bronchoscopy camera view, and the like. The user interface may be provided on a display. The display may or may not be a touchscreen. The display may be a light-emitting diode (LED) screen, organic light-emitting diode (OLED) screen, liquid crystal display (LCD) screen, plasma screen, or any other type of screen. The display may be configured to show a user interface (UI) or a graphical user interface (GUI) rendered through a software application (e.g., via an application programming interface (API) executed on the system).

In some embodiments, the user console may comprise a treatment control interface 511 and a treatment control module 503. The treatment control interface and the treatment control module may be separate self-contained components. Alternatively or in addition to, the treatment control interface and the treatment control module may be integrated single component. For example, the treatment control module may include a user input system 503 that is in communication with the treatment interface module. Alternatively, the treatment control module may be a standalone system.

The user console or a component of the user console (e.g., treatment interface module) as shown in the example 520 may be mounted to the robotic support system 523. Alternatively or in addition to, the user console or a component of the user console (e.g., treatment interface module) may be mounted to a separate mobile cart 513. The mobile cart 513 may include various elements such as rechargeable power supply in electrical communication with an electric panel providing charging ports for portable electronic devices, converters, transformers and surge protectors for a plurality of AC and DC receptacles as power source for the on-board equipment including one or more computers storing application specific software for the treatment interface module.

In some embodiments, the treatment control module 503 may include, for example, a user interface hand held device allowing physicians to control the robotic endoscope (e.g. bronchoscope) with ease. In some embodiments, the user input device or control device may be customized or personalized. Details about the portable user interface device/system are described later herein. Alternatively or in addition to, the treatment control module 503 may not be a portable device. For instance, the treatment control module may be integrated to the robotic support system.

Figure 6A:
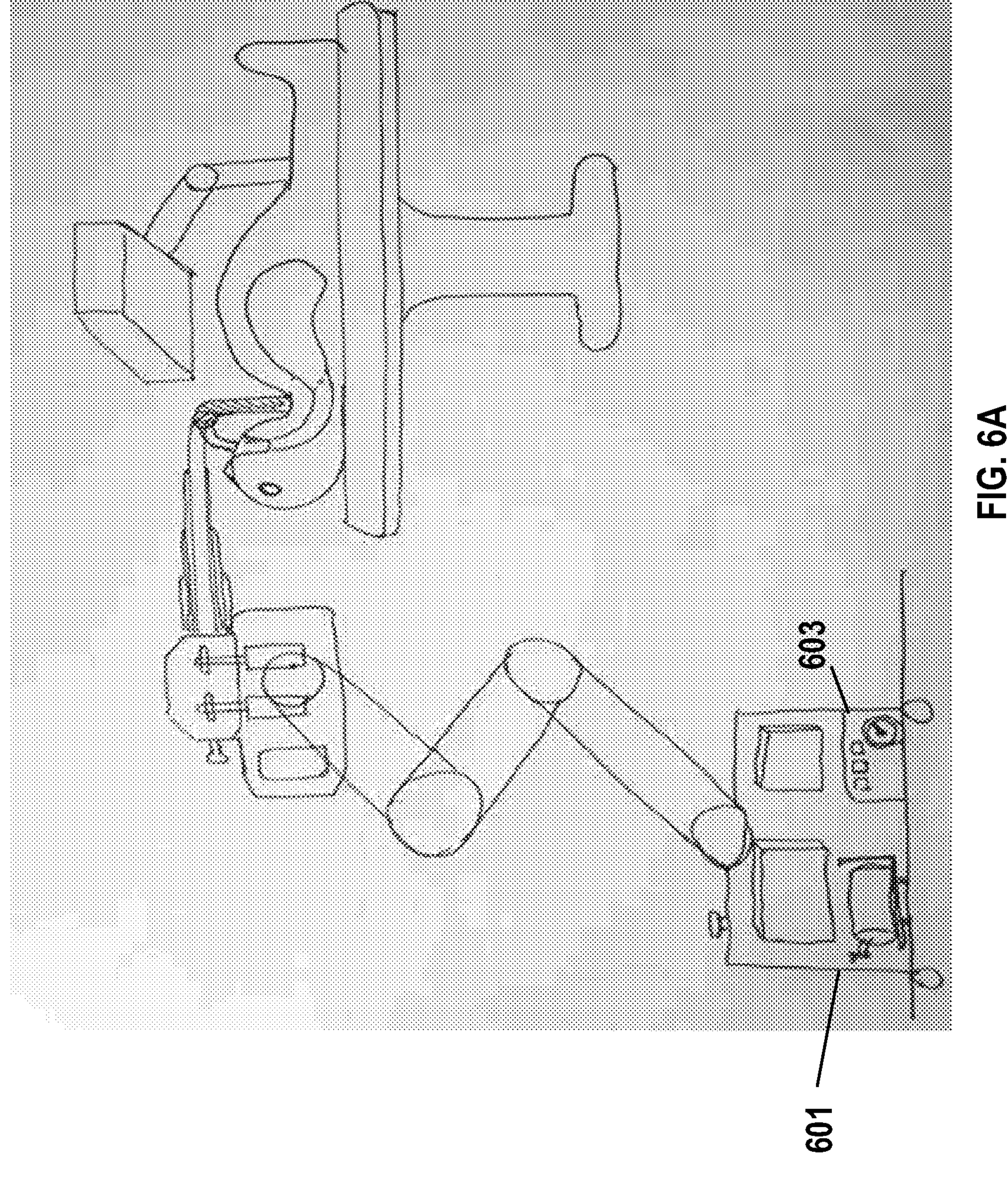
FIG. 6A and FIG. 6B show an example of a treatment control module.
Figure 6B:
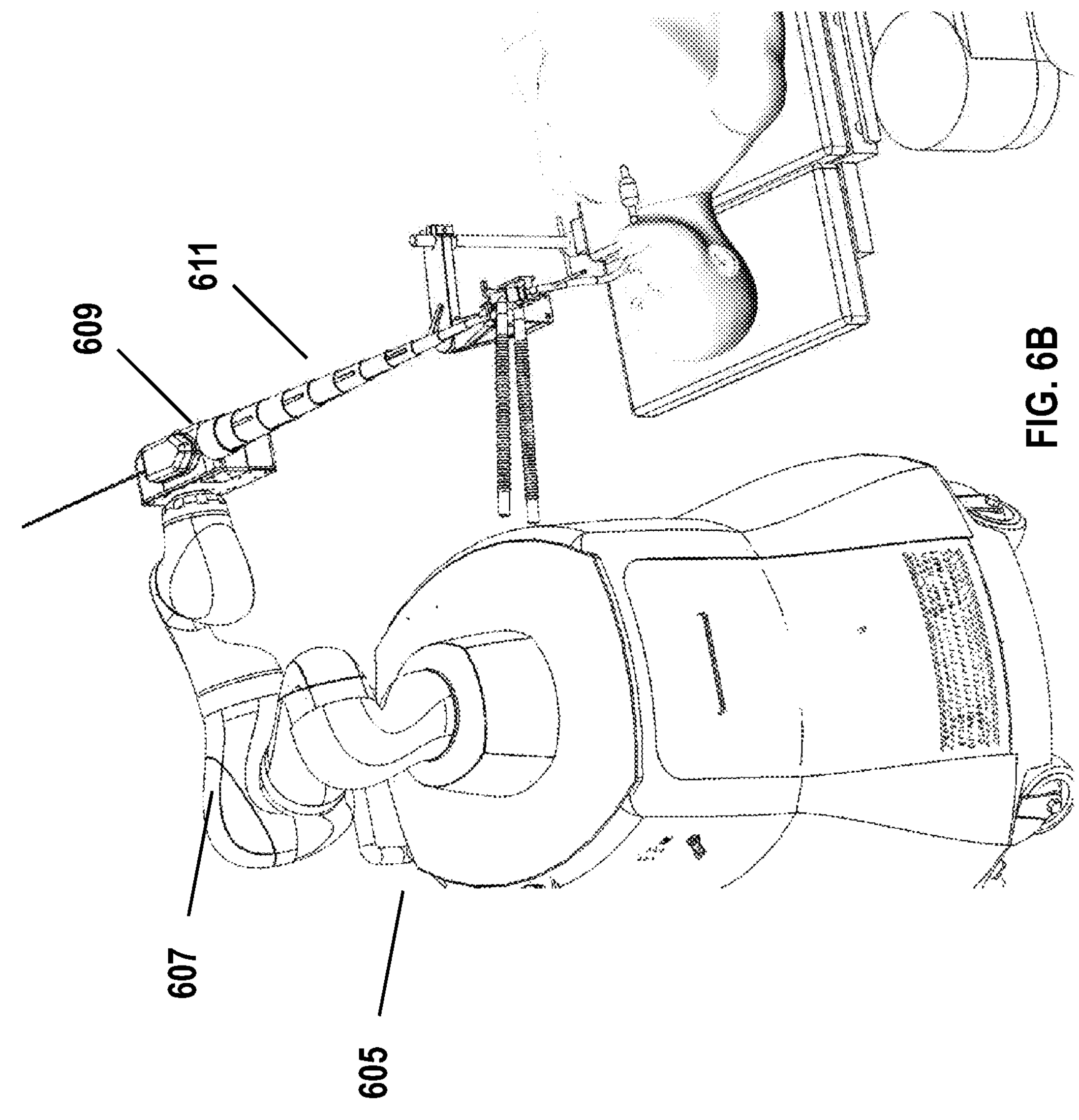

FIG. 6A and FIG. 6B show an example of a system with a treatment control system. In some embodiments, the treatment control system may include or be integrated with a robotic support system 605 including the robotic arm 607, instrument driving mechanism 609, robotic control unit, and one or more peripherical equipment's such as irrigation 601 and aspiration 603 system. The robotic arm may initiate the positioning of the robotic bronchoscope 611 or other robotic instrument. The instrument driving mechanism may be used to control the elongate member or robotic bronchoscope in two or more degrees of freedom (e.g., articulation). The irrigation and aspiration systems 601, 603 may reside on a robotic arm base cart or any other part of the system. The irrigation and aspiration system may connect to the working channel through a connector or a lure. The irrigation system can inject fluids such as saline and the aspiration system may aspire mucus or saline or other material out of the airways. In some embodiments, the irrigation and aspiration system may be used with aid of camera visualization.

Figure 7:
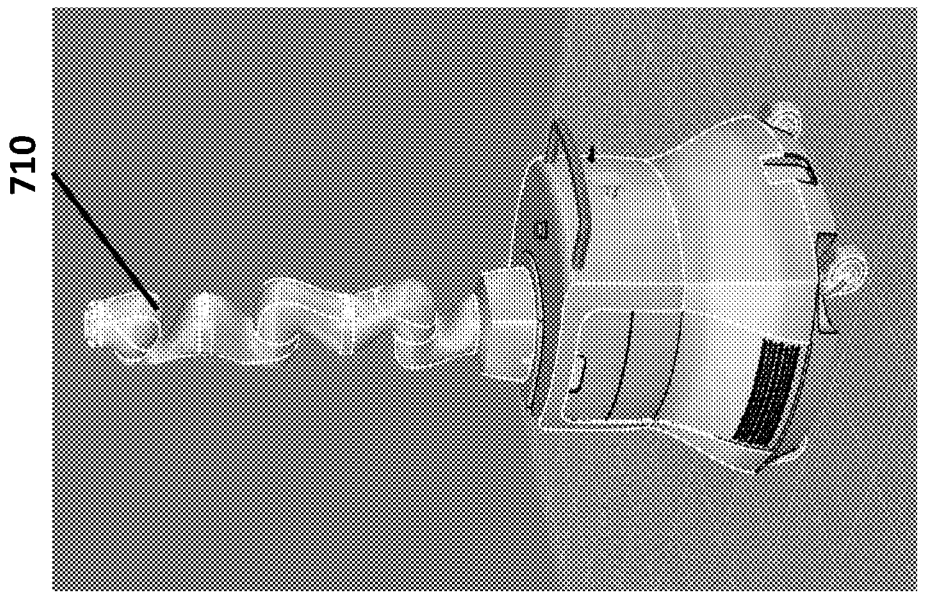
FIG. 7 shows an example of a robotic arm mounted on top of a robot cart in a treatment control module.

FIG. 7 shows an example of a robotic arm 710 mounted on top of a robot cart in a treatment control system. The robotic arm 710 may automatically position the catheter assembly to an initial position (e.g., access point) to access the target tissue. In some embodiments, the robot arm can be passively moved by an operator. In such case, an operator can push the arm in any position and the arm compliantly moves. The robot can also be controlled in a compliant mode to improve human robot interaction. For example, the compliant motion control of the robot art may employ a collision avoidance strategy and the position-force control may be designed to save unnecessary energy consumption while reducing impact of possible collisions. In some embodiments, the instrument driving mechanism may be mounted to the robotic arm. The arm may have redundant degrees of freedom allowing for its elbow to be algorithmically, or passively, moved into configurations that are convenient for an operator.

Low Cost and Single Use Robotic Bronchoscope

In one aspect of the invention, a single-use robotic bronchoscope is provided. The robotic bronchoscope can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in pre-sterilized package and are intended to be disposed of after a single-use.

Figure 2B:
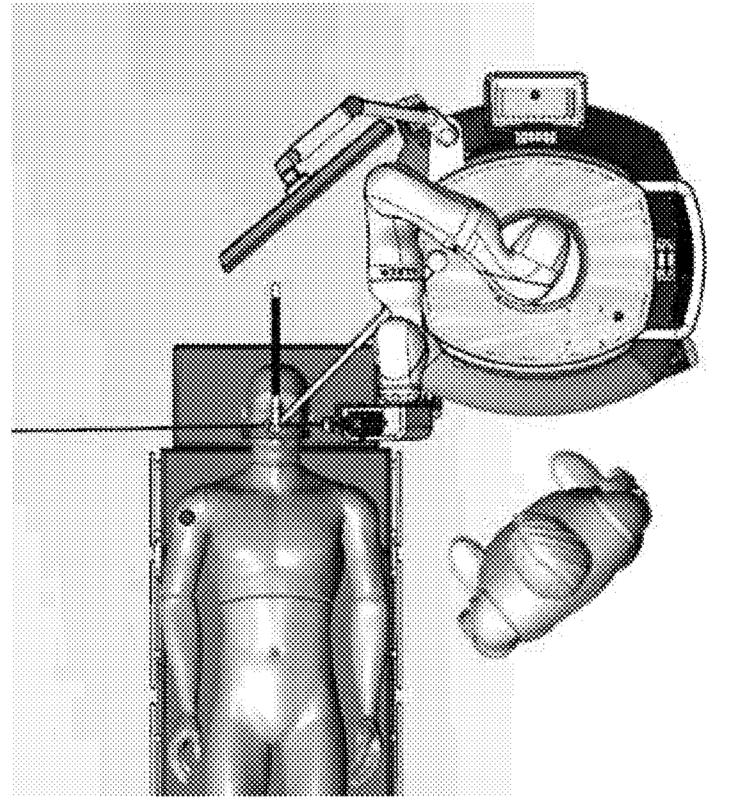
Figure 8:
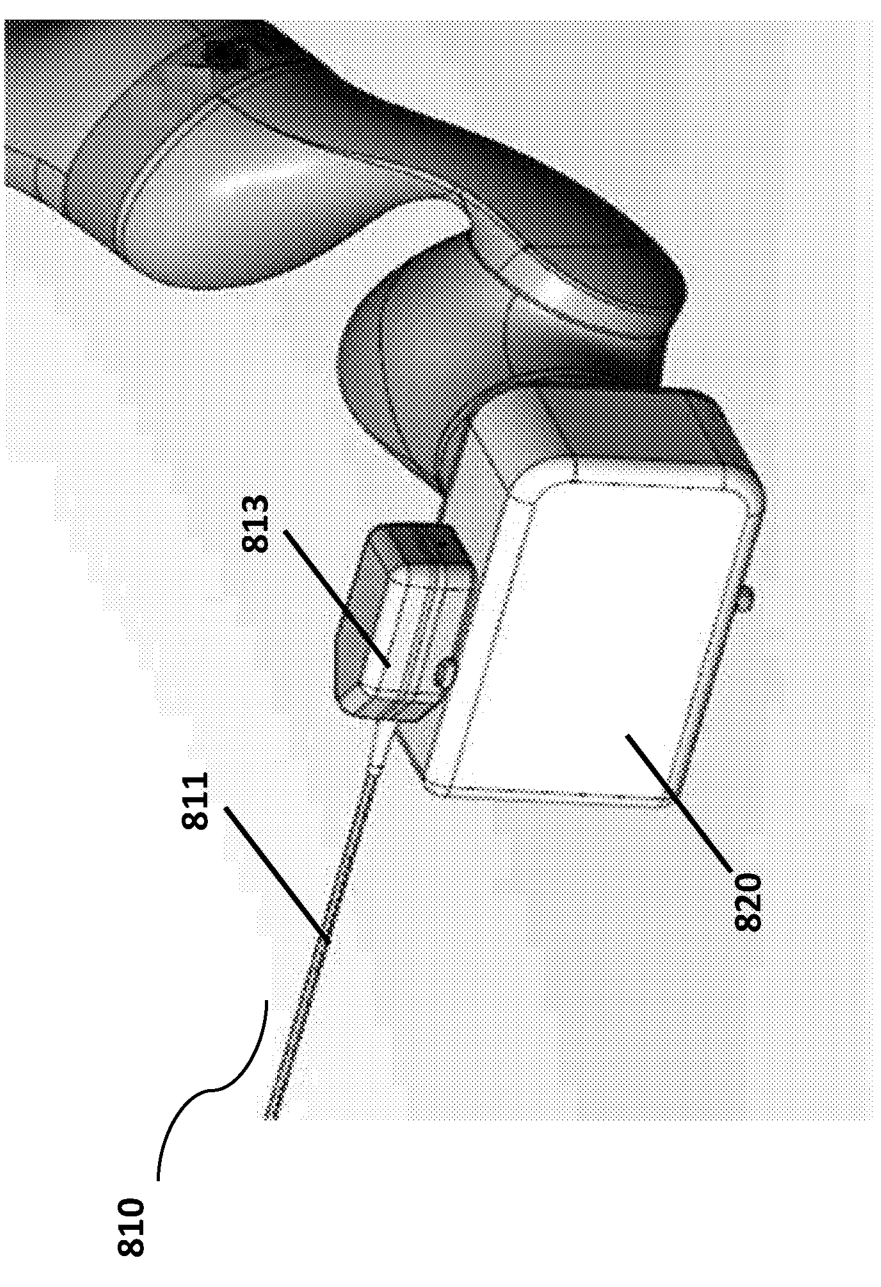
FIG. 8 shows an example of a robotic bronchoscope, in accordance with some embodiments of the invention.
Figure 9:
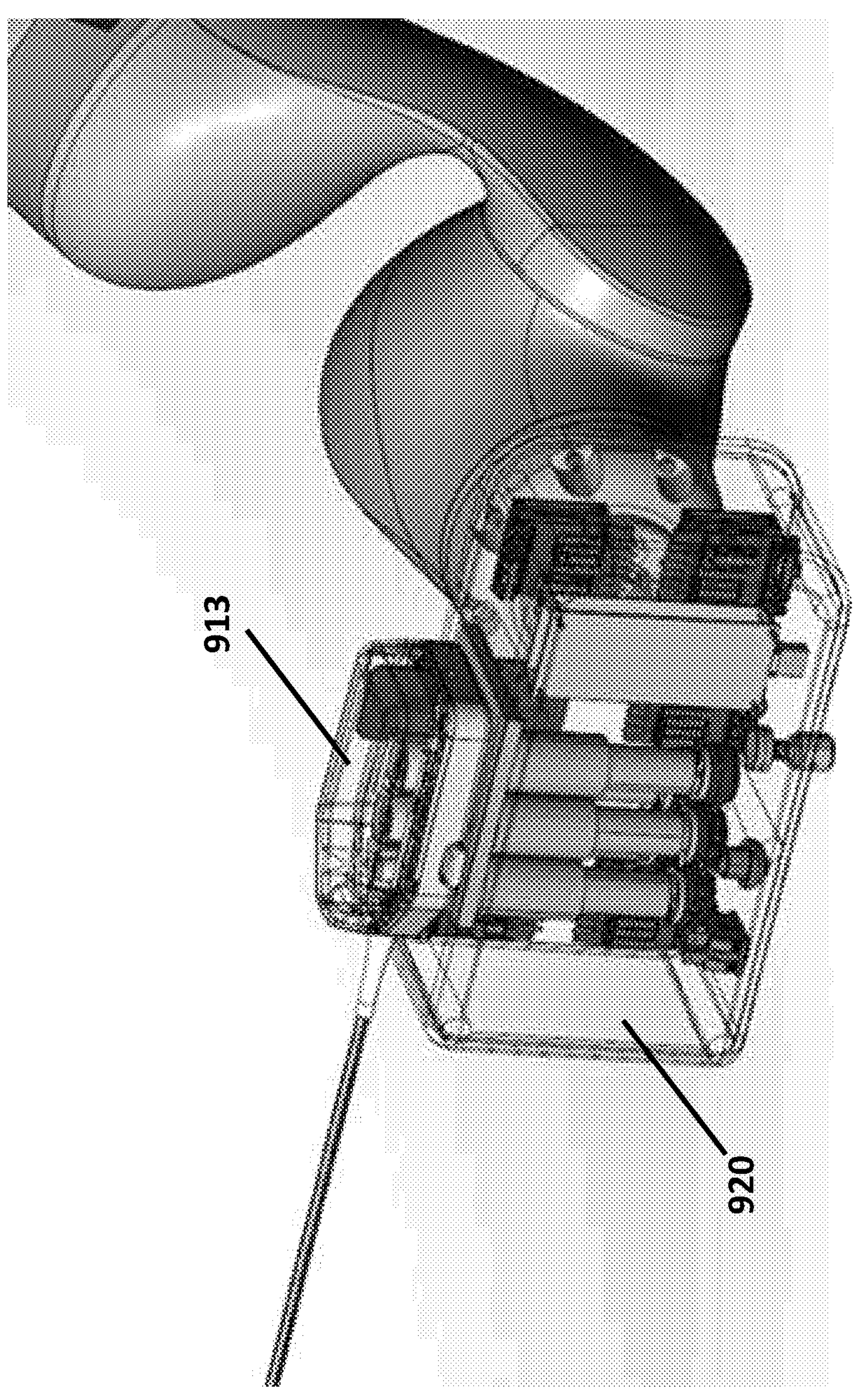
FIG. 9 shows an example of an instrument driving mechanism providing mechanical interface to a handle portion of a robotic bronchoscope, in accordance with some embodiments of the invention.
Figure 10:
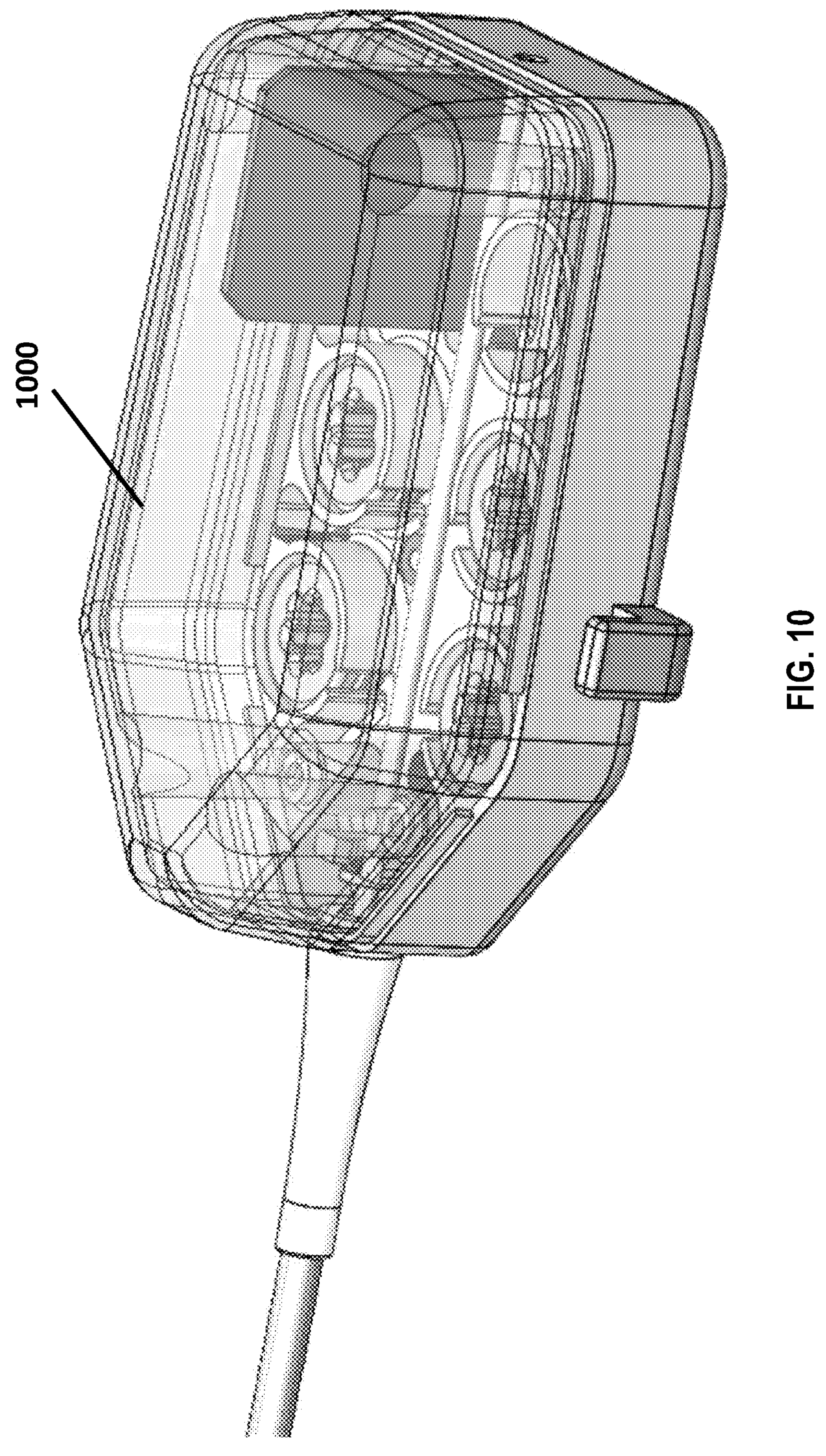
FIG. 10 shows an example handle portion of the robotic bronchoscope, in accordance with some embodiments of the invention.

FIGS. 8-10 show examples of a robotic bronchoscope, in accordance with some embodiments of the invention. As shown in FIG. 8, a robotic bronchoscope 820 may comprise a handle portion 813 and a flexible elongate member 811. In some embodiments, the flexible elongate member 811 may comprise a shaft, steerable tip and a steerable section. The robotic bronchoscope 820 can be the same as the steerable catheter assembly as described in FIG. 2. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. The bronchoscope may contain varying levels of stiffness along its shaft, as to improve functional operation.

The robotic bronchoscope can be releasably coupled to an instrument driving mechanism 820. The instrument driving mechanism 820 may be mounted to the arm of the robotic support system or to any actuated support system as described elsewhere herein. The instrument driving mechanism may provide mechanical and electrical interface to the robotic bronchoscope 820. The mechanical interface may allow the robotic bronchoscope 820 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

FIG. 9 shows an example of an instrument driving mechanism 920 providing mechanical interface to the handle portion 913 of the robotic bronchoscope. As shown in the example, the instrument driving mechanism 920 may comprise a set of motors that are actuated to rotationally drive a set of pull wires of the catheter. The handle portion 913 of the catheter assembly may be mounted onto the instrument drive mechanism so that its pulley assemblies are driven by the set of motors. The number of pulleys may vary based on the pull wire configurations. In some cases, one, two, three, four, or more pull wires may be utilized for articulating the catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as EM sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

FIG. 10 shows an example handle portion 1000 of the robotic bronchoscope, in accordance with some embodiments of the invention. In some case, the handle portion 1000 may be housing or comprise components configured to process image data, provide power, or establish communication with other external devices. In some cases, the communication may be wireless communication. For example, the wireless communications may include Wi-Fi, radio communications, Bluetooth, IR communications, or other types of direct communications. Such wireless communication capability may allow the robotic bronchoscope function in a plug-and-play fashion and can be conveniently disposed after single use. In some cases, the handle portion may comprise circuitry elements such as power sources for powering the electronics (e.g. camera and LED light source) disposed within the robotic bronchoscope or catheter.

The handle portion may be designed in conjunction with the catheter such that cables or fibers can be eliminated. For instance, the catheter portion may employ a design having a single working channel allowing instruments to pass through the robotic bronchoscope, as well as low cost electronics such as a chip-on-tip camera, illumination sources such as light emitting diode (LED) and EM sensors located at optimal locations in accordance with the mechanical structure of the catheter. This may allow for a simplified design of the handle portion. For instance, by using LEDs for illumination, the termination at the handle portion can be based on electrical soldering or wire crimping alone. For example, the handle portion may include a proximal board where the camera cable, LED cable, and EM sensor cable terminate to while the proximal board connects to the interface of the handle portion and establishes the electrical connections to the instrument driving mechanism. As described above, the instrument driving mechanism is attached to the robot arm (robotic support system) and provide a mechanical and electrical interface to the handle portion. This may advantageously improve the assembly and implementation efficiency as well as simplify the manufacturing process and cost. In some cases, the handle portion along with the catheter may be disposed of after a single use.

Single-Use Steerable Catheter

Figure 11:
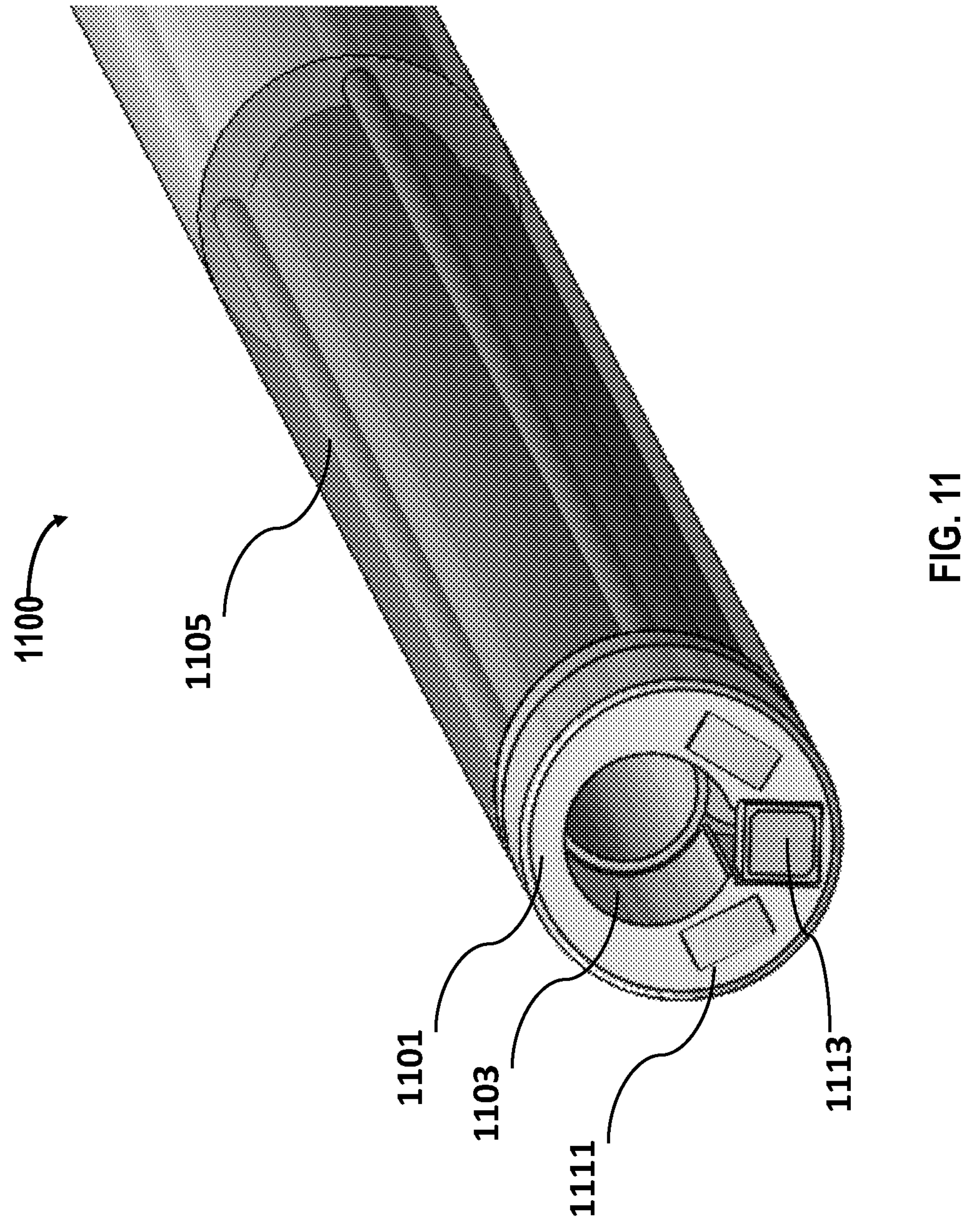
FIG. 11 shows an example steerable catheter, in accordance with some embodiments of the invention.

FIG. 11 shows an example steerable catheter 1100, in accordance with some embodiments of the invention. In some embodiments, the catheter may have a substantially integral design that one or more components may be integral to the catheter thereby simplifying the assembly, manufacturing process while preserving the kinematic, dynamic performance of the steerable catheter. As shown in the example, the steerable catheter may comprise an elongate member 1101 or a probing portion that is brought into proximity to the tissue and/or area that is to be examined. The elongate member 1101 may, in some cases, also be referred to as catheter. The catheter 1101 may comprise internal structures such as a working channel 1103 allowing tools as described elsewhere herein to be inserted through. In some cases, the working channel may have a dimension such as diameter of around 2 mm to be compatible with standard tools.

The catheter 1101 may be composed of suitable materials for desired flexibility or bending stiffness. In some cases, the materials of the catheter may be selected such that it may maintain structural support to the internal structures (e.g., working channel) as well as being substantially flexible (e.g., able to bend in various directions and orientations). For example, the catheter can be made of any suitable material such as urethane, vinyl (such as polyvinyl chloride), Nylon (such as vestamid, grillamid), pellethane, polyethylene, polypropylene, polycarbonate, polyester, silicon elastomer, acetate and so forth. In some cases, the materials may be polymer material, bio-compatible polymer material and the catheter may be sufficiently flexible to be advancing through a path with a small curvature without causing pain to a subject. In some cases, the catheter may comprise a sheath. The sheath may not be the same length of the catheter. The sheath may be shorter than the catheter to provide desired support. Alternatively, the catheter may be substantially a single-piece component.

In some case, the distal portion or tip of the catheter may be substantially flexible such that it can be steered into one or more directions (e.g., pitch, yaw). In some embodiments, the catheter may have variable bending stiffness along the longitudinal axis direction. For instance, the catheter may comprise multiple segments having different bending stiffness (e.g., flexible, semi-rigid, and rigid). The bending stiffness may be varied by selecting materials with different stiffness/rigidity, varying structures in different segments, adding additional supporting components or any combination of the above. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 1105. The distal portion of the catheter may be made of any suitable material such as co-polymers, polymers, metals or alloys such it can be bent by the pull wires. In some embodiments, the proximal end or portion of one or more pull wires 1105 may be operatively coupled to various mechanisms (e.g., gears, pulleys, etc.) in the handle portion of the catheter assembly. The pull wire 1105 may be a metallic wire, cable or thread, or it may be a polymeric wire, cable or thread. The pull wire 1105 can also be made of natural or organic materials or fibers. The pull wire 1105 can be any type of suitable wire, cable or thread capable of supporting various kinds of loads without deformation, significant deformation, or breakage. The distal end or portion of one or more pull wires 1105 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

As described above, the pull wires may be made of any suitable material such as stainless steel (e.g. SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter or the interstitials of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 1113. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1111 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 12 shows an example distal portion of the catheter with integrated imaging device and the illumination device. A camera may be located at the distal portion. For example, the camera may be embedded into a cavity 1210 at the distal tip of the catheter. The cavity 1210 may be integrally formed with the distal portion of the cavity and may have a dimension matching a length/width of the camera such that the camera may not move relative to the catheter. The camera may be adjacent to the working channel 1220 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in wire bundle providing power to the camera as well as illumination elements or other circuitry at the distal tip of the catheter. The camera and/or light source may be supplied with power from a power source disposed in the handle portion via wires, copper wires, or via any other suitable means running through the length of the catheter. In some cases, real-time images or video of the tissue or organ may be transmitted to external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 1230 having a dimension matching a dimension of the miniaturized LED light source. As shown in the illustrated example, two cavities 1230 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1231 may be placed at the forwarding end face of the distal tip providing precise positioning of the LEDs as well as sufficient room for the glue. The cover 1231 may be composed of transparent material matching refractive index of the glue so that the illumination light may not be obstructed.

Figure 13:
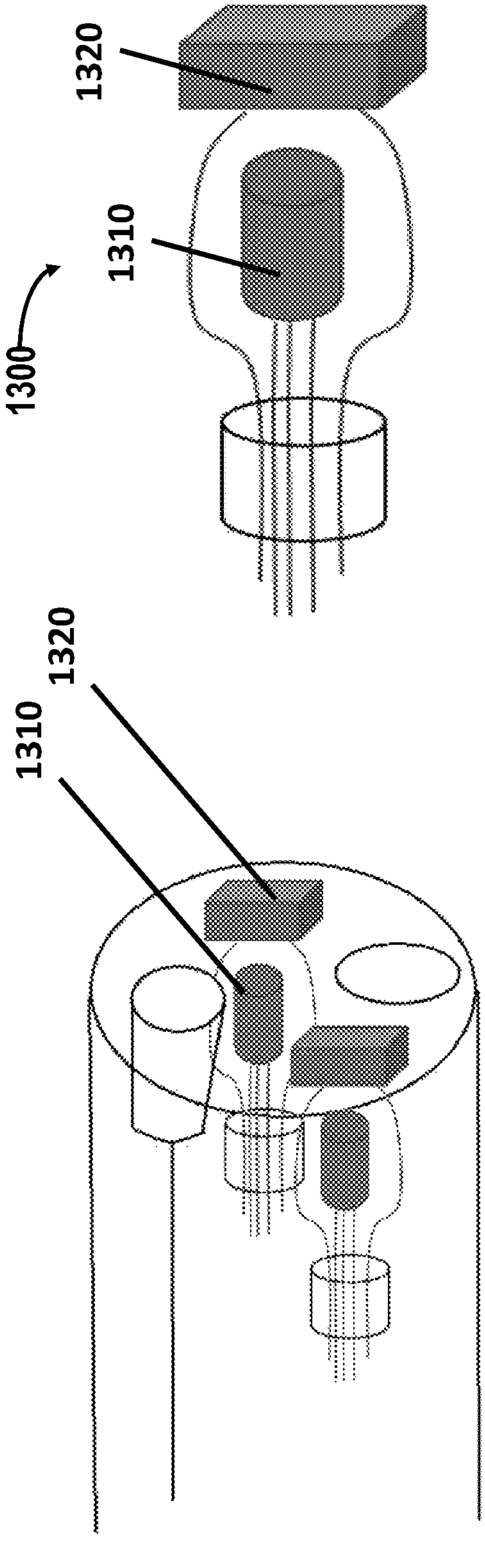
FIG. 13 shows an example of a compact configuration of a plurality of electronic elements disposed at a distal portion of a catheter, in accordance with some embodiments of the invention.

In some embodiments, one or more sensors may be embedded into the distal portion of the catheter. In conventional robotic bronchoscopes, sensors may be used to track the tip position which are usually located at the distal tip thereby causing an increased size of the tip. The provided steerable catheter may bundle one or more electronic components to provide a compact design. In some cases, the illumination light source and one or more position sensors may be combined into a bundle. FIG. 13 shows an example of a compact configuration of the electronic elements disposed at the distal portion. In some embodiments, position sensors such as electromagnetic (EM) sensors may be used to accurately track the position of the distal tip of the catheter. In some cases, one or more EM sensors 1310 may be disposed at the distal portion and may be placed adjacent to or behind the illumination light sources 1320 (e.g., LEDs) in a stereoscopic arrangement. Electromagnetic coils located on the distal end may be used with an electromagnetic tracking system to detect the position and orientation of the distal end of the endoscope while it is disposed within an anatomical system. In some embodiments, the coils may be angled to provide sensitivity to electromagnetic fields along different axes, giving the disclosed navigational systems the ability to measure a full 6 degrees of freedom: three positional and three angular.

In some cases, an EM sensor and a LED light source may form a bundle 1300. The power cables of the EM sensors may be bundled together with the wires of the LEDs to provide reduced space and complexity. In some cases, the stereoscopic alignment may provide differential 5D measurement, or a fused 6D measurement, that allows accurate positioning and orientation-sensing of the catheter distal tip. During the procedure, the EM field generator positioned next to, under, or above, a patient torso may locate the EM sensors thereby tracking the location of the catheter tip in real-time.

Pull Wire Configurations and Design

Figure 14:
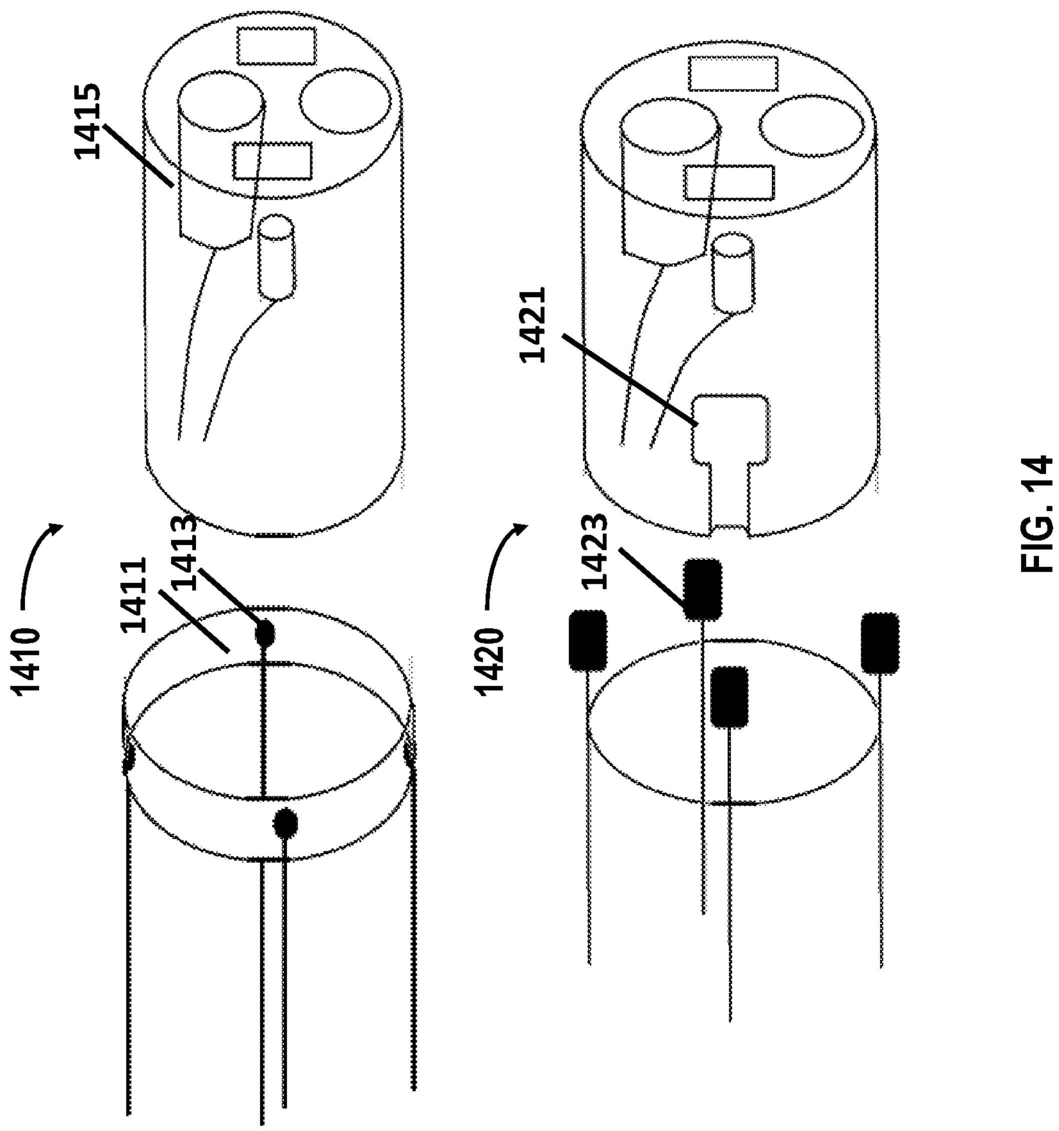
FIG. 14 shows an example of a conventional configuration of pull wires attached to a control ring structure and a novel configuration of the present disclosure.

The robotic bronchoscope may comprise one or more pull wires for controlling articulation of the catheter. In conventional endoscopes, the distal end or portion of the one or more pull wires may be anchored or mounted to a control ring, such that operation of the pull wires by the control unit may apply force or tension to the control ring which may steer or articulate (e.g., up, down, pitch, yaw, or any direction in-between) certain section or portion (e.g., distal section) of the catheter. FIG. 14 shows an example of a conventional configuration of pull wires 1413 attached to a control ring structure 1411 and a novel configuration 1420 of the present disclosure. The control ring may be attached to the distal end of the catheter 1415. Usually the tip of the pull wires is welded or soldered to the control ring 1411 and the control ring may also be attached to the distal tip by welding. The welding process can be costly, cumbersome and complex. Moreover, when one pull wire is broken or misfunctions, the entire steering control functionality may be affected.

The provided robotic bronchoscope may comprise individually controlled pull wires each of which is connected to the distal portion directly. As shown in the example 1420, the one or more pull wires 1423 may be attached to an integrally formed structure 1421 of the distal portion. For example, the integrally formed structure 1421 may be grooves that are molded with the distal tip. The grooves may have a dimension or size match the dimension of the distal end 1421 of the pull wire such that the pull wire can be conveniently crimped at distal end. This may advantageously improve the assembly efficiency. In some instances, the pull wires may be rigidly affixed to the grooves at the distal end such that the distal end of the pull wire may not be permitted to move relative to the distal portion of the catheter.

The pull wire configuration may also provide improved reliability in steering the distal portion. For instance, as each pull wire is individually connected to the distal portion and individually controlled, the articulation force may be dynamically adjusted according to different pull wire configurations. For instance, the articulation force may be recalculated and the control signals for controlling the pull wires may be dynamically adjusted based on the available pull wires in case of a pull wire is broken.

Figure 15:
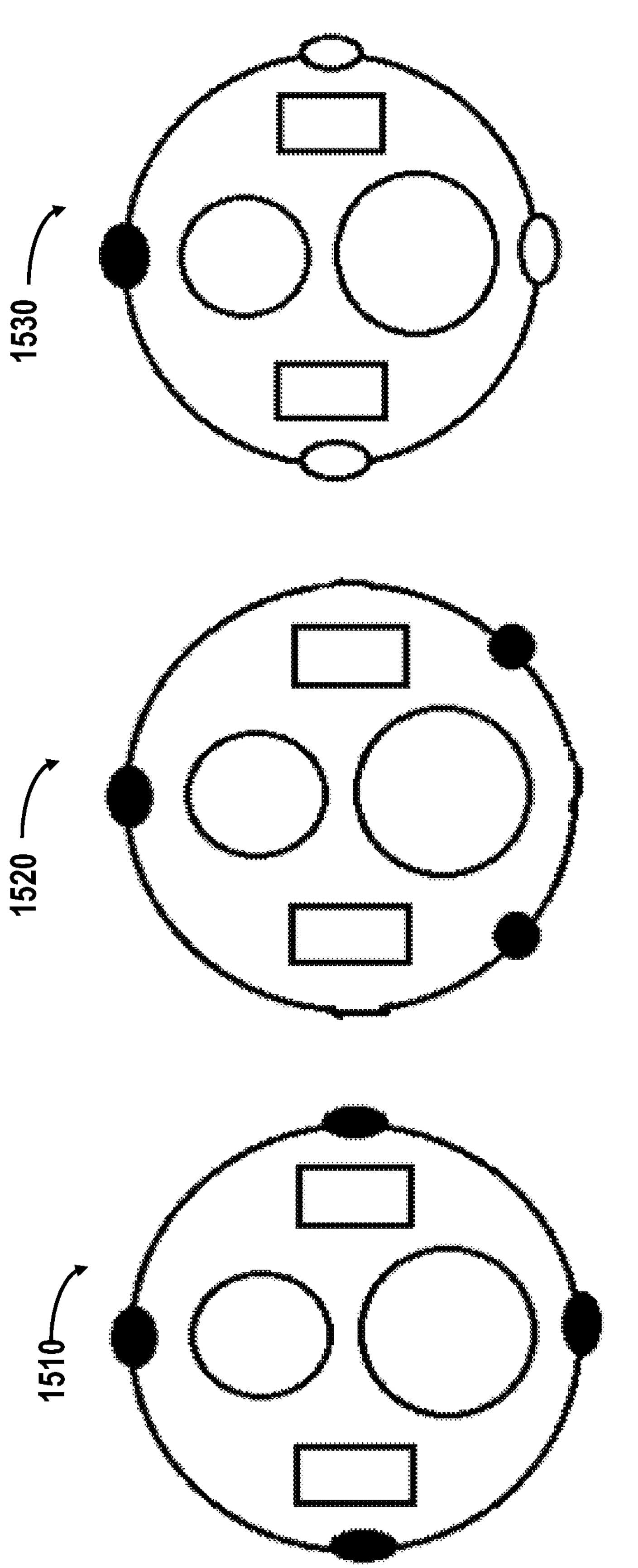
FIG. 15 shows various configurations of pull wires for a robotic catheter system, in accordance with some embodiments of the invention.

The convenient assembly of pull wires to the distal portion may also allow for flexibility in designing pull wire configurations. For example, the number or combination of pull wires can be selected or adjusted dynamically to meet different performance or design requirements. FIG. 15 shows various configurations of pull wires for a robotic catheter system. In some embodiments, the integral structure (grooves) for receiving the pull wires may be pre-fabricated. For example, four grooves may be integrally formed with the catheter and one or more pull wires may be fixedly connected/crimped to one or more grooves selected from the plurality of grooves to form different configurations 1510, 1530. As shown in the example, any number of grooves/slots or any given subset of grooves/slots can be selected to receive or couple to the pull wires at one end. In some cases, once a combination of slots/grooves is selected to be coupled to the corresponding pull wires, a pull-wire configuration pattern may be formed and a mapping relationship between the selected grooves/slots and the pull wires may be transmitted to the control unit. Control signals may then be generated during articulation based on the mapping relationship to achieve desired articulation force.

In another example, the pre-fabricated grooves may have various configurations. For instance, a three-pull-wire configuration 1520 may have three grooves separated by about 120°. In some cases, a virtual mapping algorithm may map the three-wire configuration to a four-wire configuration. The virtual mapping algorithm can also be utilized to update a new mapping relationship when one or more pull wires are misfunctioning/broken during operation. The virtual mapping algorithm maps a selected configuration pattern to an updated configuration pattern upon a change of the state of the one or more pull wires. Such integral design of the pull wire configurations advantageously simplifies the assembly, manufacturing process while preserving the kinematic, dynamic performance of the catheter.

Guidewire with an Inflatable Tip

In some embodiments, a guidewire may be used during bronchoscopy operation. A guidewire may usually be inserted far beyond the tip of the bronchoscope to enter the desired air passageway first, and subsequently allow the bronchoscope to slide over the guidewire into the selected passage. Due to the guidewire's smaller diameter in comparison to that of a bronchoscope, the guidewire may not have sufficient stiffness and/or enough frictional force to anchor the guidewire within the air passages.

Figure 16:
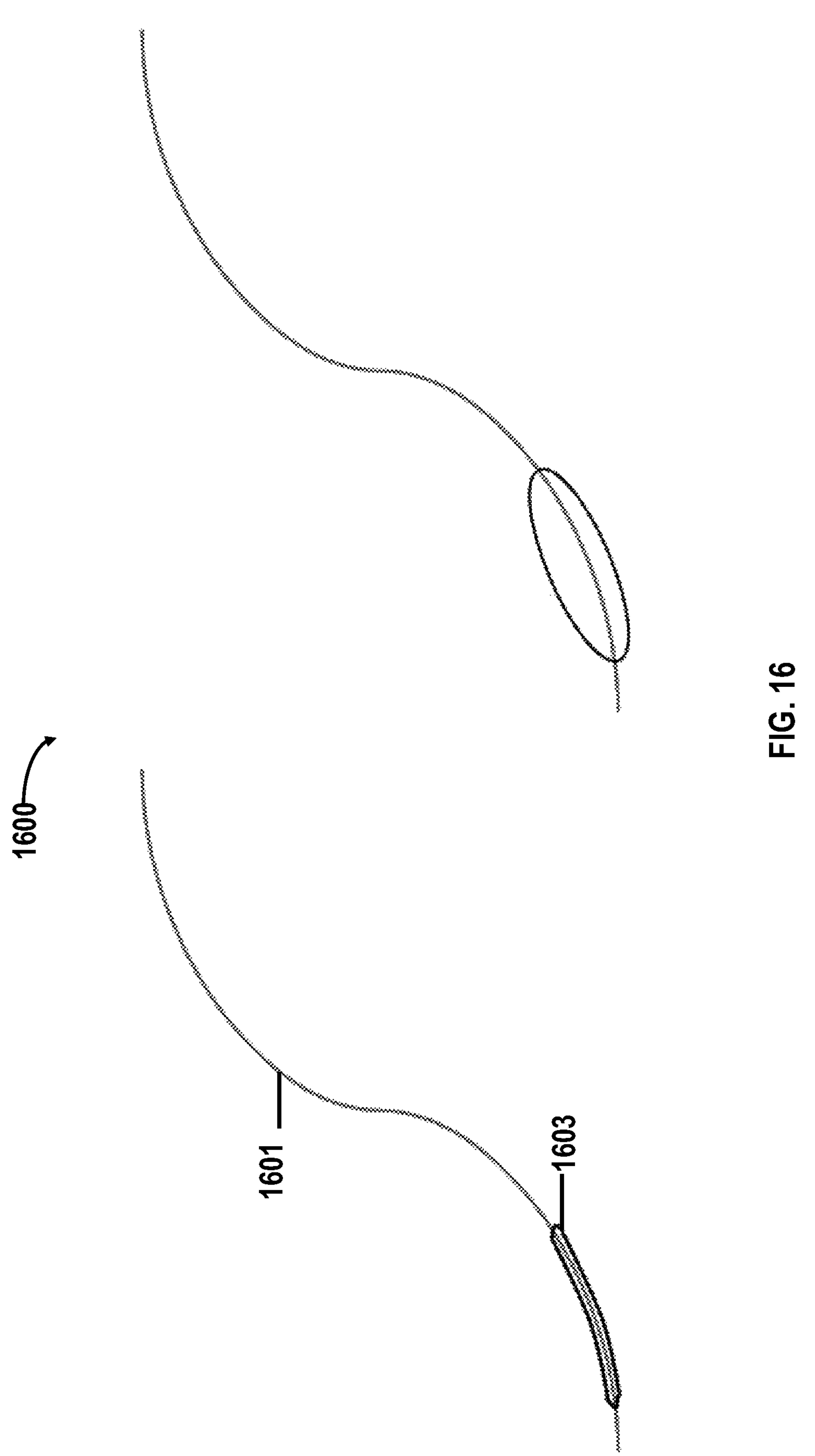
FIG. 16 shows an example of a guidewire with inflatable tip, in accordance with some embodiments of the invention.

The guidewire of the present disclosure may have an expandable outside diameter feature at the tip. FIG. 16 shows an example of a guidewire 1600 with inflatable tip. The guidewire 1601 may be inserted through the working channel of the catheter/bronchoscope to assist in navigation of the air passages in the lung. In some cases, the guidewire may be extended past the tip of the catheter into the desired airway and the catheter may then slide over the guidewire to reach the desired location. The inflatable tip can be implemented using various suitable methods. For example, an additional component 1603 such as an inflatable balloon may be positioned at or close to the distal end of the guidewire. The balloon may be connected through the working channel to a balloon inflation source or pump for inflation or deflation of the balloon.

In some cases, the guidewire may comprise perforated holes. The diameter of the deflated balloon may be equal to the diameter of the elongate arm (e.g. bronchoscope catheter). In some cases, the diameter of the deflated balloon may be slightly greater than the elongate arm. The guidewire may be able to move distally or proximally. The guidewire may be attached to an air pump to inject and withdraw the air from the guidewire, which consequently inflates and deflates the balloon respectively. During the insertion of guidewire into airway, the balloon may remain deflated. while the proper location is reached, the balloon will be inflated by pumping in the air. Once the bronchoscope reaches the desired forward position, the balloon may be deflated by pumping the air out that may allow the guidewire to move forward. In some embodiments, the inflatable tip can be made of collapsible mesh structures using materials, such as shape memory alloy (SMA), electro-active polymer (EAP), and ferromagnetic fluids, with its corresponding inflation and deflation control mechanisms. The anchoring element can have any other form to secure the anchoring of the guidewire. For example, the anchoring element may be metal wires that can expand or collapse radially. The anchoring element may be actuated by a slide actuator that is slid linearly to cause the anchoring element to change its position and in particular, to cause the anchoring element to either deploy or to be placed back into a collapsed position. The sliding action of the actuator may be translated into a change in the position (condition) of the anchoring element (e.g., anchoring element deploys and radially expands so as to provide a structure that anchors the guidewire in place, or conversely, anchoring element radially contracts and is returned to a collapsed state.

Anti-Buckling Device

In some embodiments, the catheter may be designed to be flexible. When the flexible portions of catheter are inserted by extending mechanisms through bronchoscope into patients, one or more sections may bend or buckle. In such cases, to prevent the catheter from buckling while the bronchoscope is advanced towards the patient, an anti-buckling mechanism may be coupled to the handle portion of the robotic bronchoscope to support the catheter. Although, anti-buckling mechanisms such as telescoping mechanisms are known, the flexible portions of catheter may still bend or buckle. Existing anti-buckling devices may comprise a plurality of cylindrical elements that are open end at both ends. The diameter of the cylindrical elements may increase gradually. These cylindrical elements may be coupled together and can collapse or expand within each other. The diameter of the cylinder with smallest diameter is larger than the diameter of the elongate member therefore the elongate member can move forward when the cylinders are extended. The diameter difference allows for the catheter to not be retrieved when the anti-buckling device is retracted or removed. However, the catheter may still buckle in the segments where the diameter of the telescoping mechanism is greater than the outer diameter of the catheter.

Figure 17:
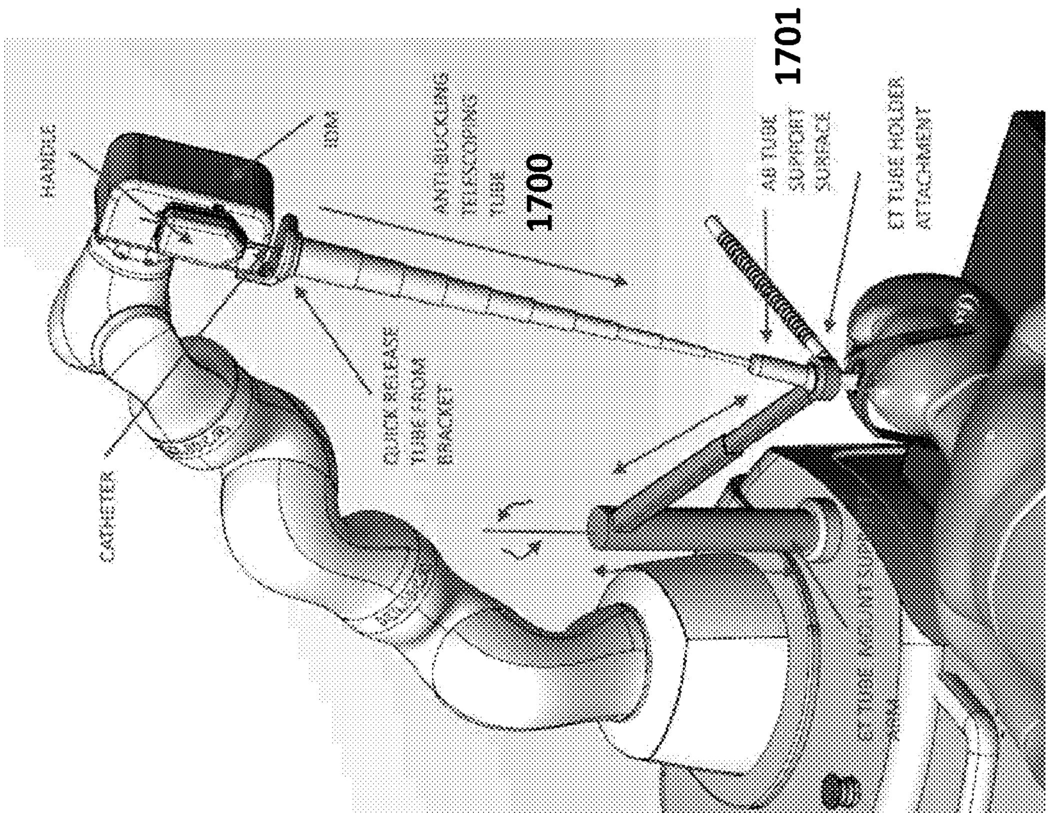
FIG. 17 shows an example anti-buckling mechanism, in accordance with some embodiments of the invention.

The present disclosure provides an improved anti-buckling mechanism. The anti-buckling mechanism is used for preventing buckling of the insertion shaft. FIG. 17 shows an example anti-buckling mechanism 1700, in accordance with some embodiments of the invention. The anti-buckling mechanism 1700 may be a telescopic extending device with internal mechanism to achieve anti-buckling of catheter during the insertion and withdrawal. The anti-buckling mechanism 1700 may be detachably connected to the handle portion of the robotic bronchoscope at one end, and may be detachably connected to a support surface 1701 at the other end. As shown in the example, the anti-buckling tube may be attached to a bracket on the instrument driving mechanism and may be removable and disposable after the procedure via quick release mechanism. A support arm may be supported by the robotic mobile cart that supports the endotracheal tube mount and provides a support surface for the distal end of the anti-buckling tube to press against as it is compressed. The support arm may be controlled to rotate, translate vertically up and down and/or may a boom arm that expands and contracts, such that it can be precisely positioned over the patients mouth and attached to the endotracheal tube mount. The support arm positioning may be synchronized with the movement of the robotic arm that it may track the location of the point of entry of the catheter.

Figure 18A:
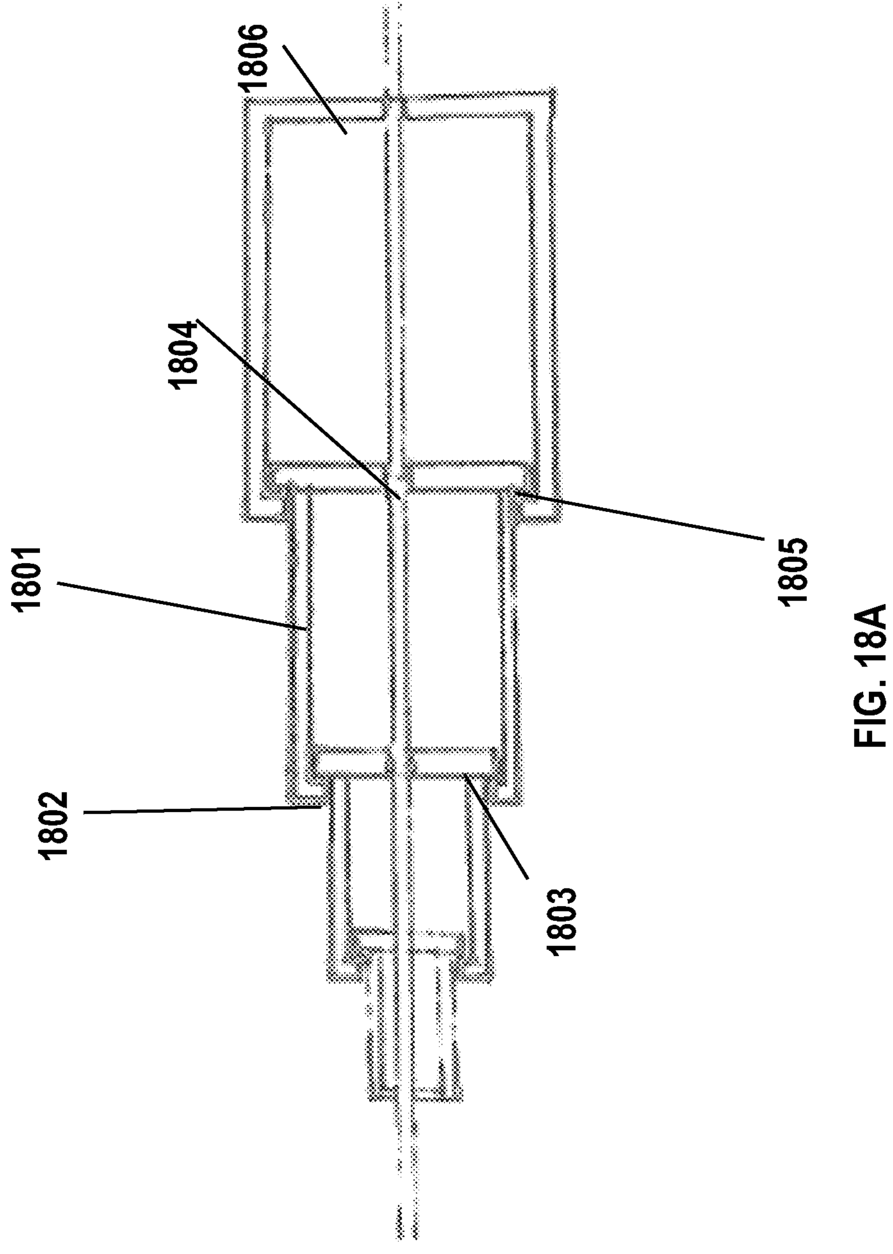
FIG. 18A shows an internal structure of an example anti-buckling mechanism, in accordance with some embodiments of the invention.

The anti-buckling mechanism may be designed with internal features to prevent the catheter from buckling. FIG. 18A shows an example of the internal structure of the anti-buckling mechanism, in accordance with some embodiments of the invention. In some cases, the anti-buckling mechanism can be a separable device that can be disposed of after single use. The anti-buckling device may include a plurality of cylinders 1801 with gradual reduction in cylinder diameters. The cylinders may be concentrically assembled or connected along the axial axis. Each cylinder may consist of a thin wall cylinder 1801, a proximal end with an inner lip 1802, a proximal closing 1803 with a clearance hole of the diameter 1804 slightly larger than catheter/sheath. The diameter of the clearance hole for all of the cylinders may be the same so that the movement of the catheter may be restricted in the cross-section plane relative to the anti-buckling device. The cylinder element may also comprise an outer stopping lip 1805 (i.e. a radial protrusion slightly larger than the outer diameter of the cylinder), and a stopper 1806 at the distal opening of the cylinder structure. In some embodiments, the proximal closing 1803 and the outer lip 1805 may be an integral single element. Alternatively, the proximal closing 1803 and the outer lip 1805 may be separately assembled together. In some embodiments, if the proximal closing 1803 and the outer lip 1805 are an integral single piece, they may be in the form of a disk, assembled at the proximal end of the cylinder element. In some cases, the proximal closing 1803 and the outer lip 1805 may be integrally formed with the cylinder element. The inner lips and the outer stopping lips may prevent the detachment of the cylinders during extending the anti-buckling device.

The clearance holes located at the center of the proximal disks may allow the catheter to slide smoothly along the driving axis, and when telescope is extended, may provide normal compression to prevent bending or buckling of the catheter. In some embodiments, the telescope can be filled with pressurized viscous fluids (e.g. silicon oil, buffer solution) to prevent rapid buckling event during large force insertion. Two attachment add-ons (plates) may be provided at the both distal and proximal ends of the entire anti-buckling device, with proximal attachment plates fastening to the robotic arm. The distal plate may be attached to a fixture that is fastened to the patient's bed through an add-on feature. In some embodiments, the fixture can be a post fastened to the bed in which case no extra force may be imposed to the patient when the anti-buckling device collapses. In the other embodiments, the fixture can be a railing on the bed.

Figure 18B:
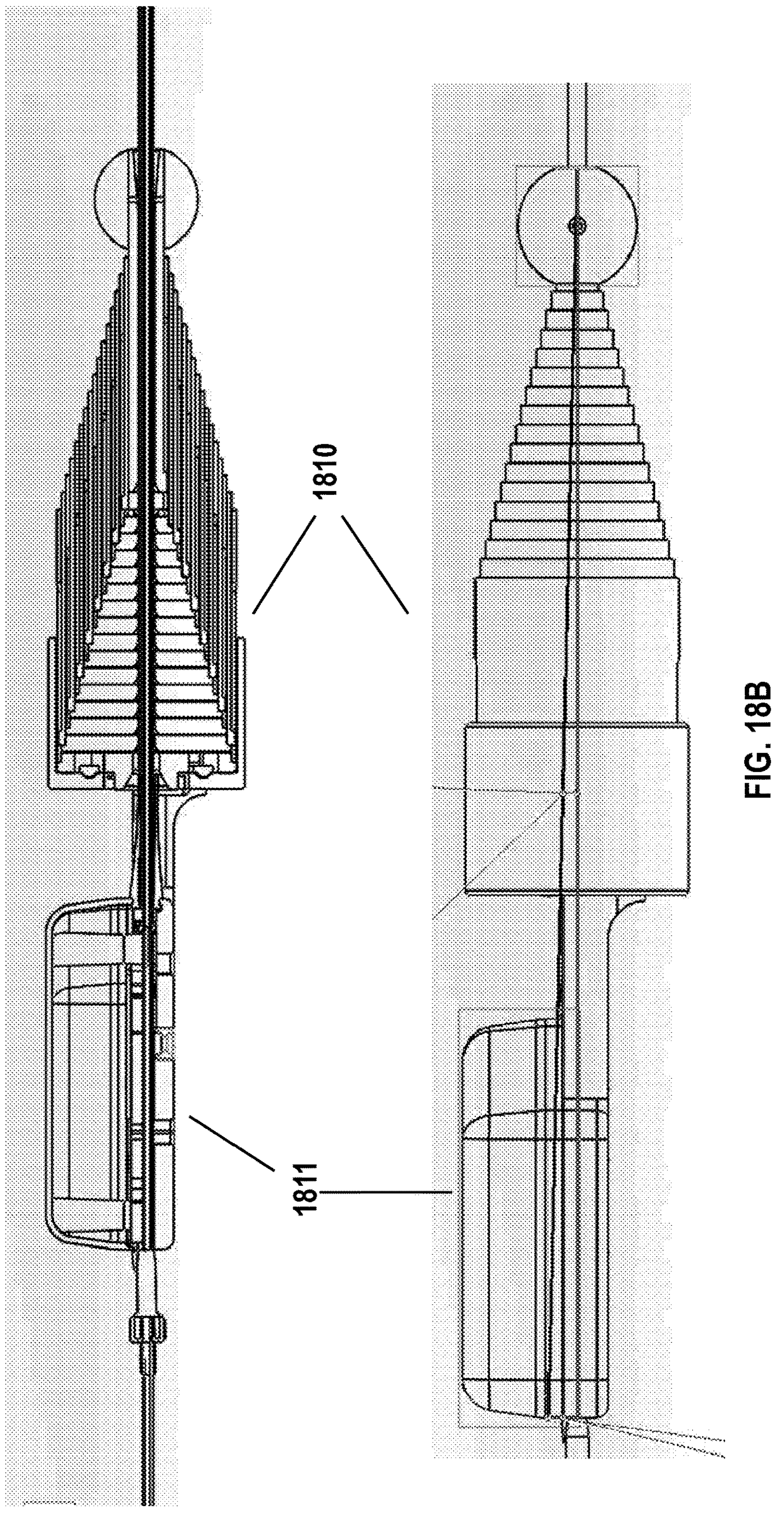
FIG. 18B and FIG. 18C show examples of an assembly of the anti-buckling mechanism and a handle.
Figure 18C:
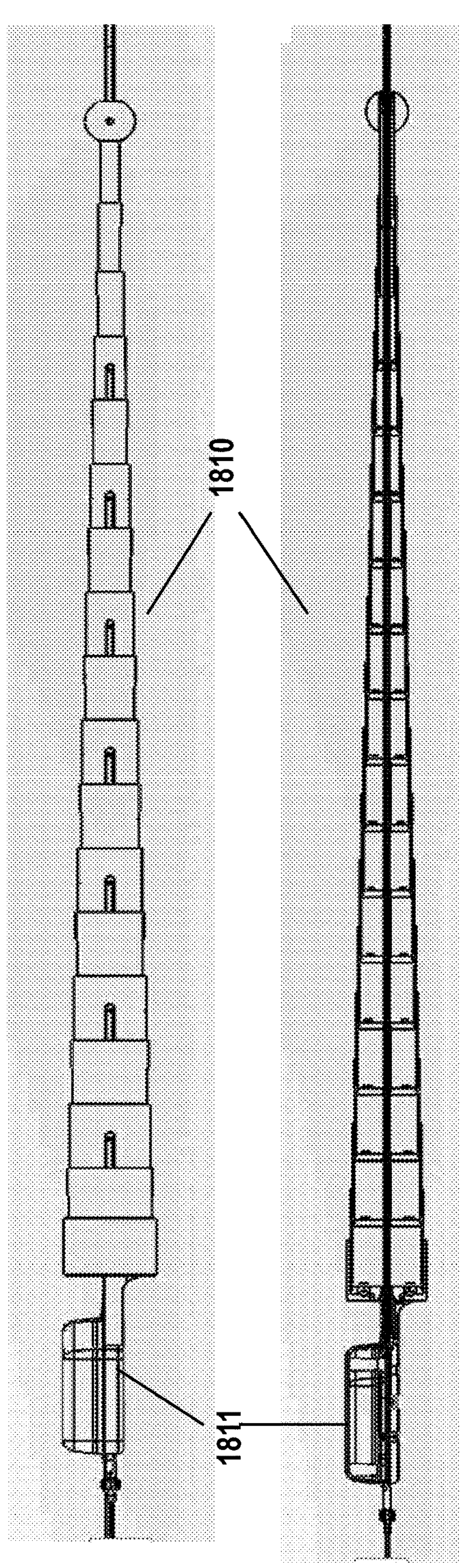

FIG. 18B and FIG. 18C show examples of an assembly of the anti-buckling mechanism 1810 and a handle 1811. FIG. 18B shows the anti-buckling mechanism is connected to a handle and in a retracted state and FIG. 18C shows the anti-buckling mechanism is fully extended.

Figure 18D:
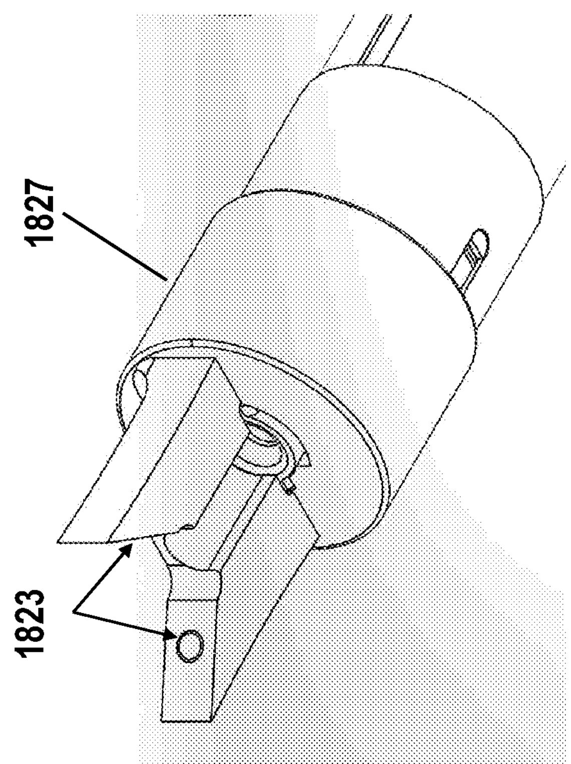
FIG. 18D shows an example of scope handle and anti-buckling tube assembly with a side-connection feature.
Figure 18D:
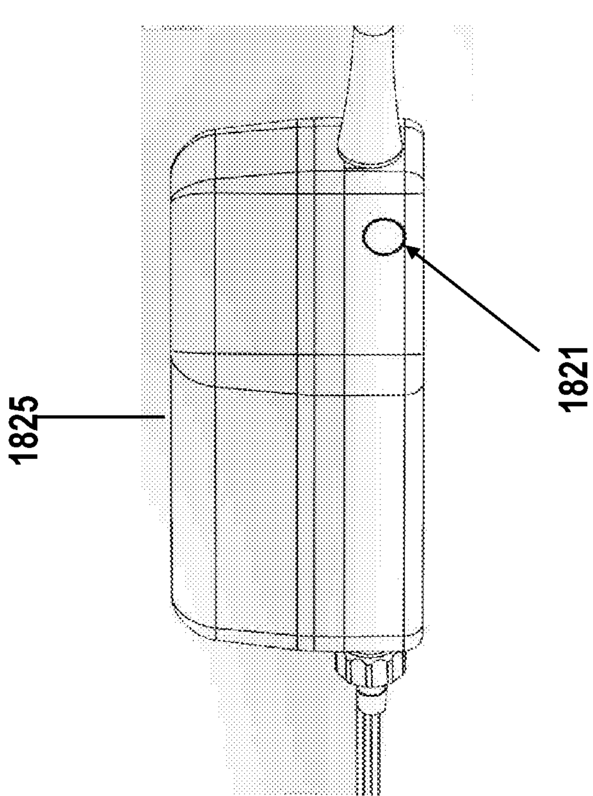
Figure 18D:

In some cases, the system and devices herein may allow for a simplified set-up flow for assembling the anti-buckling mechanism and the endoscope. For example, the anti-buckling mechanism and scope handle may be assembled via a lateral connection between the anti-buckling mechanism and the scope handle and top-load the assembled pieces as a single piece onto the instrument driving mechanism. This convenient assembly capability beneficially allows coupling the scope handle and anti-buckling assembly to the robotic arm regardless the state and current position of the instrument driving mechanism. FIG. 18D shows an example of scope handle and anti-buckling tube assembly with a side-connection feature. The anti-buckling tube 1827 can be releasably connected to the handle 1825 via a side connection feature 1821, 1823. The connector on the scope handle 1821 may be laterally attached to the corresponding connector on the anti-buckling mechanism 1823 to connect the two separate pieces. In some cases, the connector may be on both sides of the handle to be connected to the two connectors on the anti-buckling mechanism. Any suitable mechanism (button, pin, snap, magnets) may be utilized to releasably couple the anti-buckling tube to the handle. The assembled anti-buckling mechanism and handle is shown in FIG. 18E.

Figure 18E:
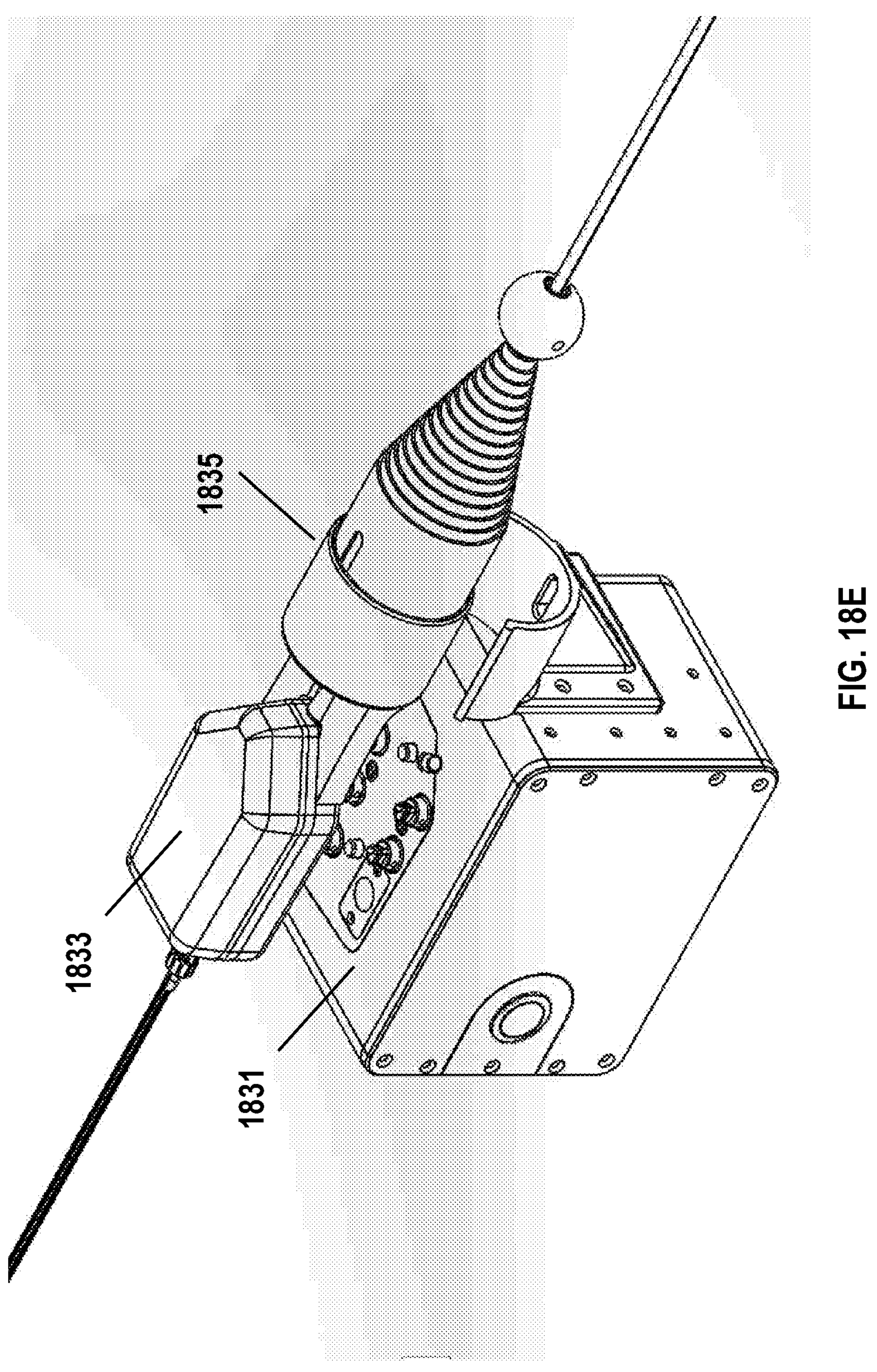
FIG. 18E illustrates an example of top-loading the connected assembly of anti-buckling tubes and scope onto an instrument driving mechanism.

FIG. 18E illustrates an example that allows a user to place the connected assembly of anti-buckling tubes 1835 and scope onto the instrument driving mechanism 1831 via the interface of the handle 1833. Assembling the scope, and anti-buckling mechanism prior to loading it onto the instrument driving mechanism may simplify the workflow.

Figure 18F:
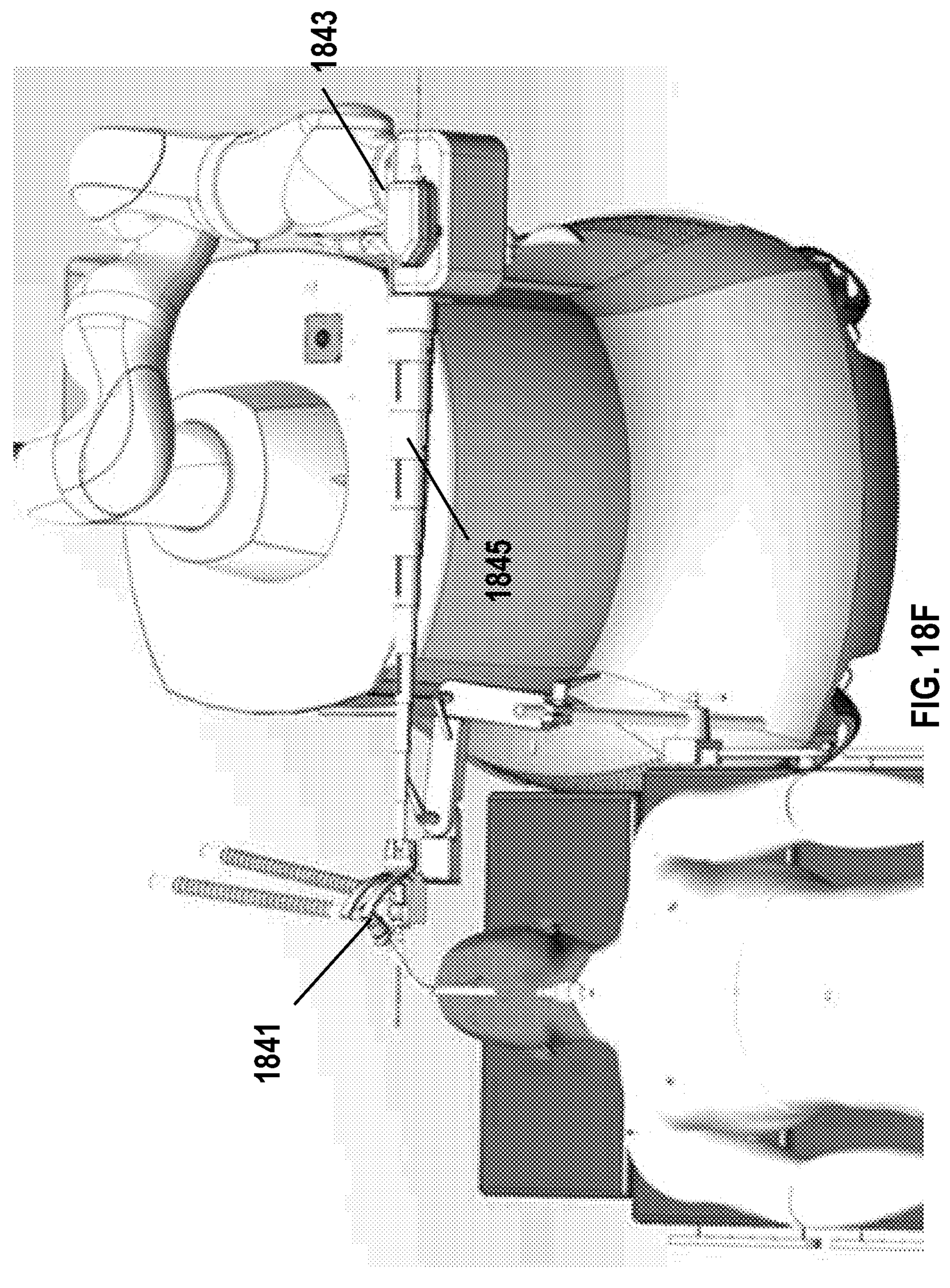
FIG. 18F shows an example of a patient side connector and IDM.
Figure 18G:
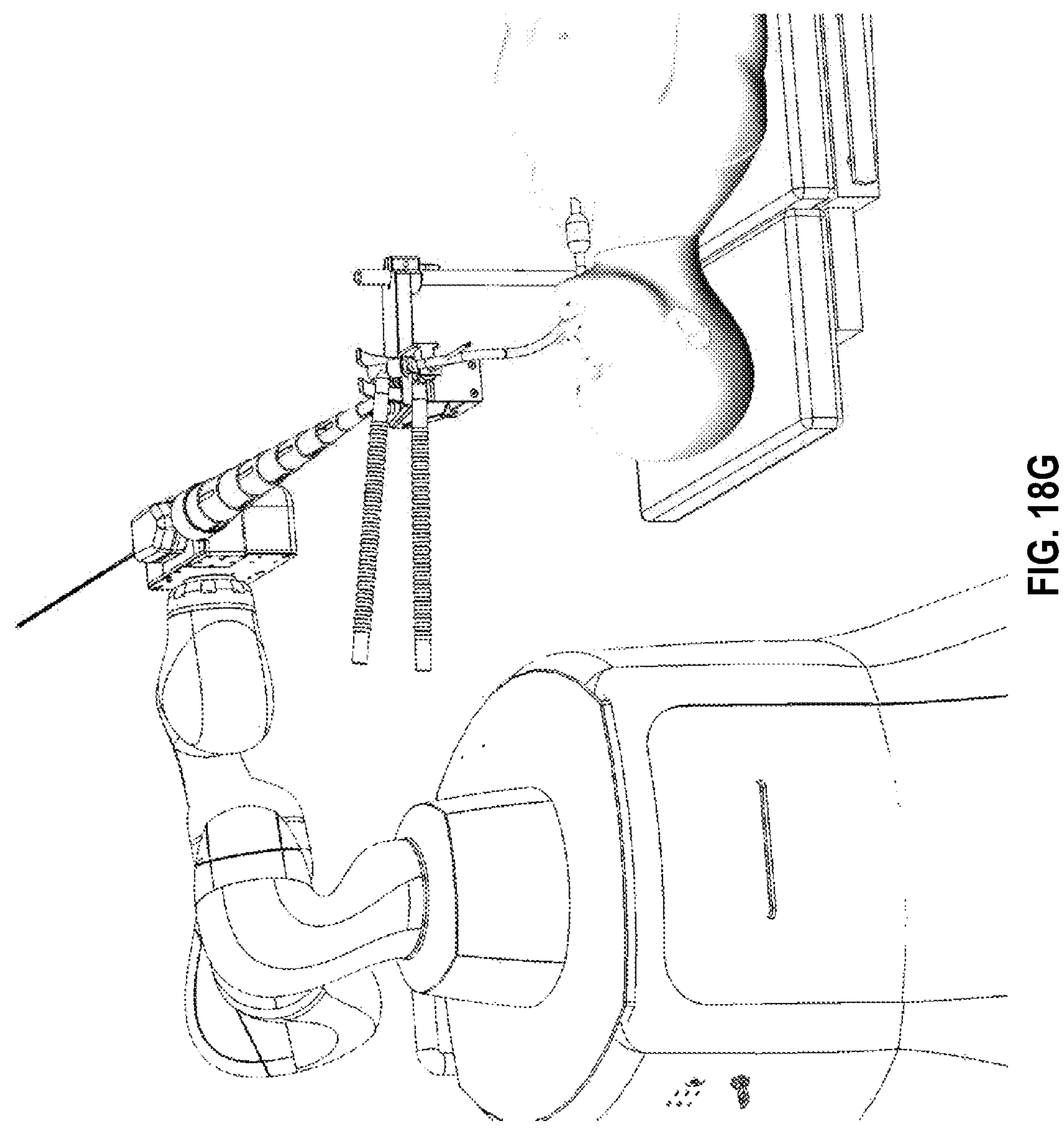
FIG. 18G shows another example of the anti-buckling mechanism traveled to the target location via the alignment between the patient-side connector and the IDM.

The anti-buckling mechanism may require a relatively linear trajectory to be traveled. In some cases, such trajectory may be ensured via an alignment between the anti-buckling mechanism in a collapsed state and a patient-side connector. FIG. 18F shows an example of a patient side connector 1841 and IDM 1841. For example, the patient-side connector may be fixed to a patient side mount (e.g., attached to the patient bed). The alignment workflow may involve lining up a collapsed anti-buckling mechanism 1845 with the patient-side connector with alignment guidance or feedback. For example, a user may be assisted with aligning the instrument driving mechanism (IDM) to the patient-side connector and be provided with feedback (e.g., visual/tactile/audible feedback) that the anti-buckling mechanism and patient-side connector are properly aligned. FIG. 18G shows another example of the anti-buckling mechanism traveled to the target location via the alignment between the patient-side connector and the IDM.

Figure 18H:
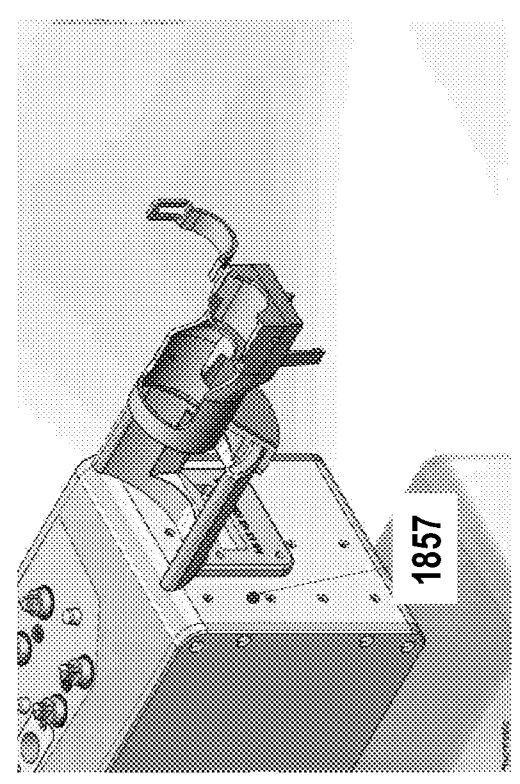
FIG. 18H and FIG. 18I show examples of alignment features.
Figure 18H:
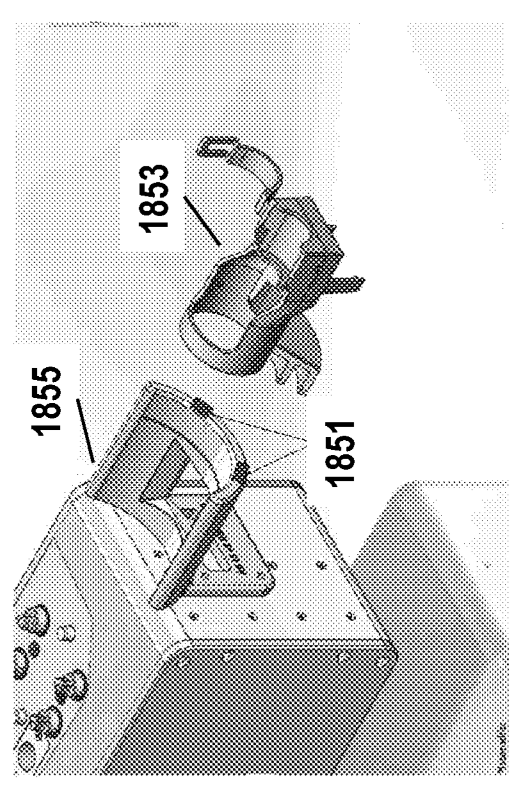

In some cases, the alignment process may be performed with the IDM and a connector on the anti-buckling patient side, prior to attaching the anti-buckling mechanism. In alternative cases, the alignment process may be performed with the anti-buckling mechanism attached. The alignment feature may include using a click alignment, laser alignment, magnets, visual indicator or tactile/audible feedbacks. FIG. 18H shows examples of alignment features 1851, 1857. In the illustrated example, mechanical alignment features such as click buttons or magnets may be provided on the patient-side connector 1853 and the IDM 1855 to provide feedback indicator about the alignment. For instance, when the alignment is completed that the click button or magnets may trigger a tactile, audible or visual signal indicating a proper alignment. In some cases, visual indicators such as colored dots/markings, slots, ridges, and the like may be provided on the IDM to assist the alignment.

Figure 18I:
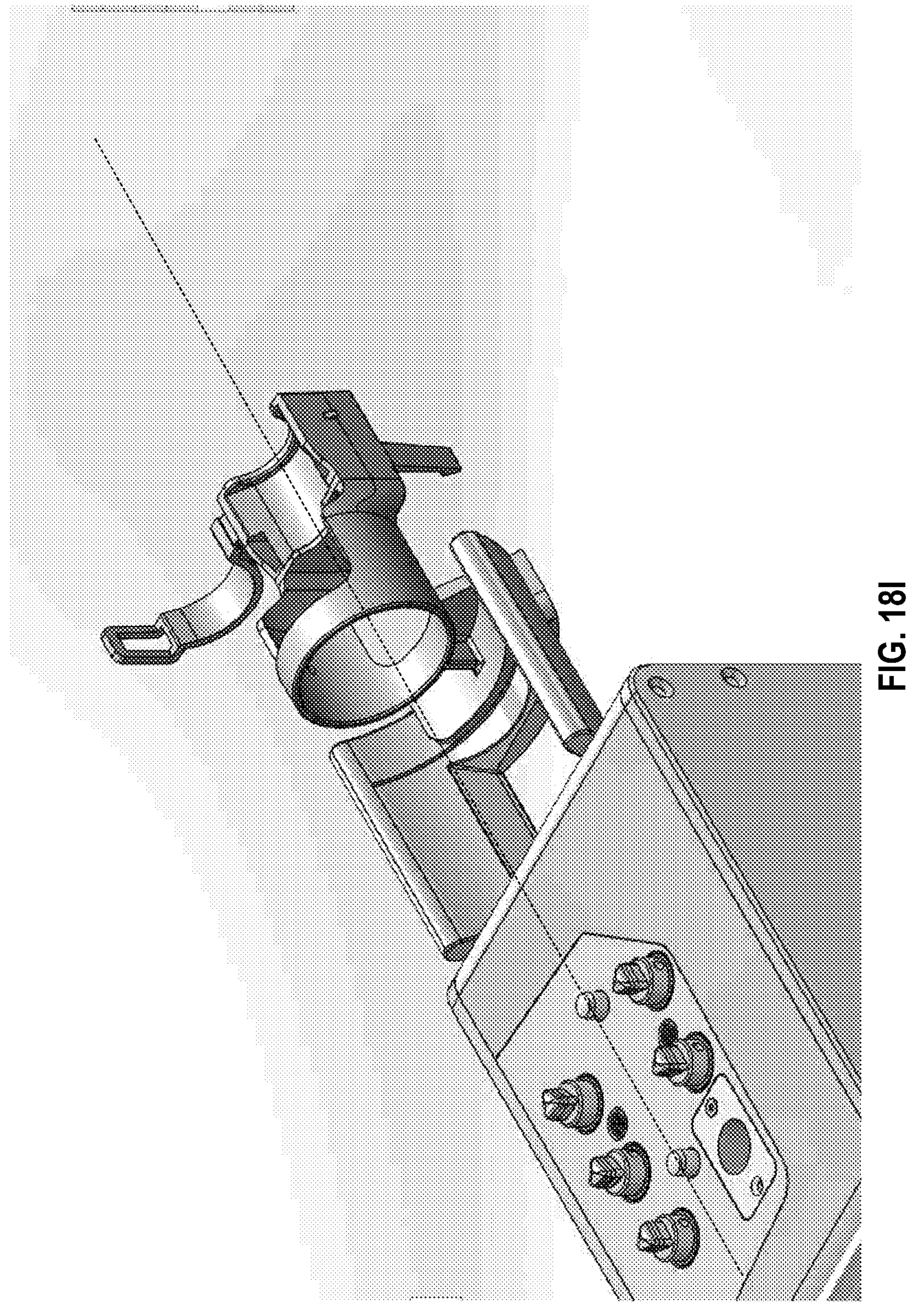

As illustrated in FIG. 18H, a laser 1857 on the IDM may be used to target the patient-side connector in order to ensure a straight-line alignment to the patient-side connector. As shown in FIG. 18I, magnets on the distal end of the anti-buckling mechanism and the patient-side connector may assist the alignment and provide visual/tactile feedback to a user that the components have been properly aligned.

User Interface

Figure 19:
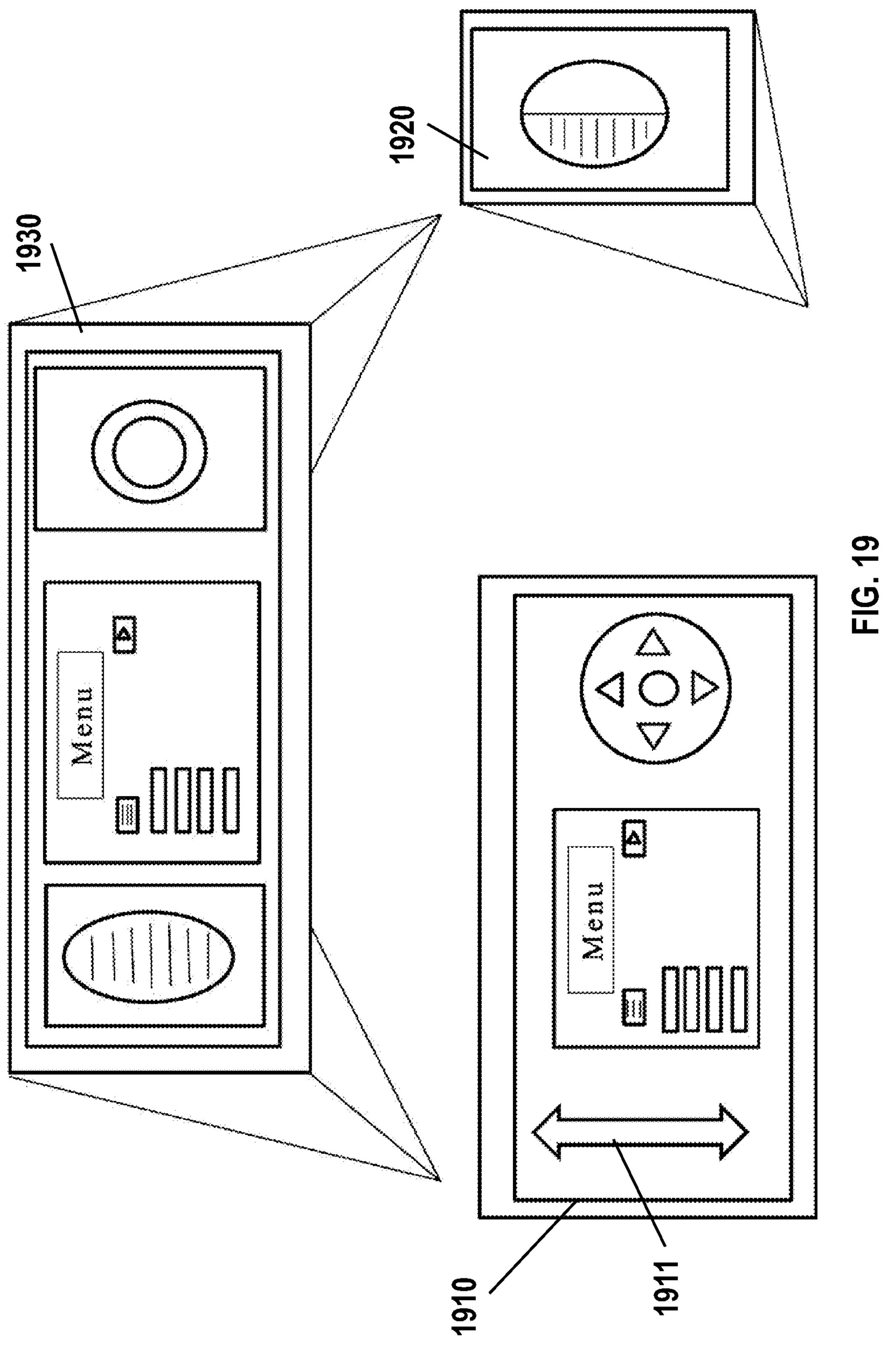
FIG. 19 shows examples of user interfaces, in accordance with some embodiments of the invention.

The user interface may include various devices such as touchscreen monitors, joysticks, keyboards and other interactive devices such as shown in the example of FIG. 19. In some embodiments, a user may be able to navigate and/or control the motion of the robotic arm and the movement of the catheter using a user input device. The user input device can have any type user interactive component, such as a button, mouse, joystick, trackball, touchpad, pen, image capturing device, motion capture device, microphone, touchscreen, hand-held wrist gimbals, exoskeletal gloves, or other user interaction system such as virtual reality systems, augmented reality systems and the like. In some cases, the user input device may be a tactile stylus device being physically in contact with a touch-sensitive display screen and the user may control the robotic system by moving the tactile stylus device on the display screen.

In some embodiments, the treatment control module may be a hand-held controller 1930. The treatment control module may comprise a proprietary, personalized or customized user input device. In some cases, one or more add-on elements 1910 may be removably coupled to an existing user device 1920 to improve user input experience of a treatment control module 1930. For instance, one or more physical user input devices or add-on elements 1920 (e.g., trackball, joystick or roller) may be coupled to a graphical user interface (GUI) 1910 provided on a user device via tactile sense or Bluetooth. For instance, a trackball, joystick or roller 1920 may replace or supplement the function of at least one of the virtual graphical element (e.g., navigational arrow, slider bar 1911) displayed on a graphical user interface (GUI) by giving it similar functionality to the graphical element which it replaces. The add-on elements may be coupled to the GUI via a physical contact in the touch screen, via an IO port, wired or wireless communication such that the user input received via the add-on elements can be mapped to an input received by the virtual graphical elements rending on the GUI. Examples of user devices may include, but are not limited to, mobile devices, smartphones/cellphones, tablets, personal digital assistants (PDAs), laptop or notebook computers, desktop computers, media content players, and the like. Details about the user interface device and user console are described later herein.

In another example, the user input device may be a camera (e.g., imaging sensor located at the display) and the user input may include retinal information, such as where the user is looking. user input to confirm new alignment of the virtual component with target locations (e.g., by squeezing a trigger or pushing a button on the laparoscopic handheld controller, voice command, etc.). Orientation of virtual components (e.g., rotational orientation of a shaft) may be adjusted with a touchpad, trackball, or other suitable input on the laparoscopic handheld controller or other device. a user device In some embodiments, the user may be permitted to personalize the user interface based on the personal preferences of the user such as handedness or the speed of driving the user interface device (e.g. the speed of moving a lever on a joystick for driving a robotic elongate member forward or backward). Artificial intelligence methods such machine learning or deep learning may be used to personalize a user interface device based on user behavior. As an example, a machine learning method may be used to learn based on the user behaviors such as the use of buttons, use of levers, the frequency of used of buttons or levers, the number of clicks or the speed of moving the levers on a joystick to adapt and become specialized. For example, the user interface may be adapted to use a combination of buttons or levers for a specific task based on user preference for using those buttons and levers.

In some embodiments, training data may comprise historic user interface interaction data or simulated data. The artificial intelligence algorithm may be trained to adapt to the user behaviors and interactions with the user interface.

In some embodiments, the training data may comprise historic user interface interaction data or simulated user interaction data as well as imaging and or video data of the procedure as described elsewhere. The user interface interaction data may be time stamped and annotated with regards to real time imaging data to distinguish the specific interaction of the user while driving the elongate member. Having a combined training dataset may allow the artificial intelligence algorithm to verify the level of experience of the user, in which case the user interface may not only adapt to the user's movements, it may also assist in training the user by for example visual or audio messages to guide the user in driving the elongate member.

Figure 20:
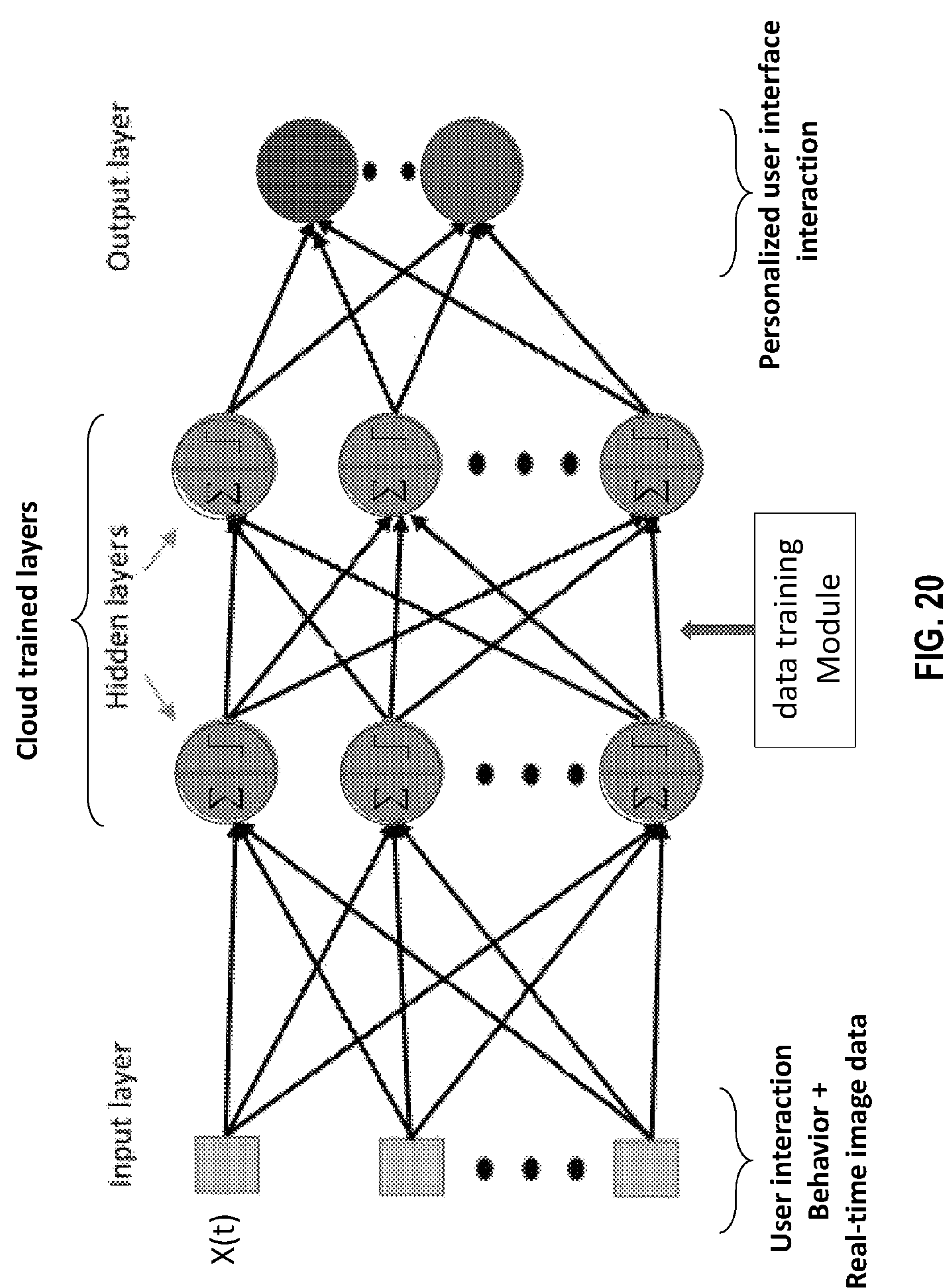
FIG. 20 shows an example of a neural network model for generating control signals in response to individual user input.

Various artificial intelligence models such as but not limited to neural networks can be implemented. An artificial intelligence model may be a trained model or trained machine learning algorithm. The machine learning algorithm can be any type of machine learning network such as: a support vector machine (SVM), a naïve Bayes classification, a linear regression model, a quantile regression model, a logistic regression model, a random forest, a neural network, convolutional neural network (CNN), recurrent neural network (RNN), a gradient-boosted classifier or repressor, or another supervised or unsupervised machine learning algorithm (e.g., generative adversarial network (GAN), Cycle-GAN, etc.) FIG. 20 shows an example of a neural network model for generating control signals in response to individual user input. Various typed of neural network can be used. The neural network may support deep learning. The neural network may be a convolutional deep neural network and/or a recurrent neural network using supervised or unsupervised training. In some embodiments, the neural network may support reinforced learning.

The input to the neural network may comprise the user interaction and behavior with regards to the user interface device such as shown in the example of FIG. 20. The input may also include the time stamped, real time image and/or video data depicting the operation and driving of the elongate member by the user. The neural network may extract features from the input data, depicting the user preferences in using various aspects of the user interface of the user interface device. For example, the user preference in using the buttons versus the lever, the handedness of the user, the speed of moving of the levers by the user, etc.

The output layer of the neural network may include one or more output nodes. Each output node may be a represent a decision based on the user behavior with regards to interaction with the user interface device and driving the elongate member. The output may output the likelihood of different actions that the user may take. Based on the location of the elongate member, one or more actions may have likelihood that is higher than a predetermined threshold. In some embodiments, based on real time image data and the location of the tip of the elongate member and the likelihoods presented by the output of the neural network, visual and/or audio indications may be displayed on a graphical user interface guiding the user to take an action, for example, stop driving the elongate member, change the driving angel, speed up or down the driving, use pull wire to bend the tip of the elongate member in a certain direction, etc. The neural network may also personalize the functionality of the elements of user interface device such as personalizing the use of certain touch buttons, push buttons or the levers on a joystick or any other user interface device.

The training datasets may be stored on a local storage such as a local memory or local server. The training dataset may also be stored on a remote dataset such as a cloud server. The training may be done online or offline. The training dataset may be updated in real time to improve the learning and functionality of the neural network.

In some cases, the platform may provide deep learning models with continual training or improvement after deployment. The deep learning models provided by the platform may be dynamically adjusted and tuned to adapt to different individuals, different surgical operations over time. The predictive model provided by the platform may be improved continuously over time (e.g., during implementation, after deployment). Such continual training and improvement may be performed automatically with little user input or user intervention.

In some embodiments, the provided robotic endoluminal platform may employ an edge intelligence paradigm that data processing and prediction/inference is performed at the edge or edge gateway (e.g., bronchoscope, robotic system, user device) while the predictive models may be built, developed and trained on a cloud/data center and run on the user device or control device (e.g., hardware accelerator) for inference. In some cases, the deep learning model may be pre-trained on the cloud and transmitted to the user device, control system or edge computing system for implementation. In some cases, the deep learning model may go through continual training as new sensor data and user feedback are collected. The continual training may be performed on the cloud or on the server. In some cases, sensor data may be transmitted to the cloud which are used to update the model for continual training and the updated model (e.g., parameters of the model that are updated) may be downloaded to the local or edge system (e.g., bronchoscopy system, robotic system, user device, software application of the bronchoscopy system) for implementation.

Portable Handheld Add-On Module

Robotic bronchoscopes are designed to be working with a robotic platform. The electronics and mechanical motions of the catheter are controlled via the robotic platform. However, at the beginning of the procedures, physicians may have the need of inspecting the main airways through the bronchoscope manually. The present disclosure provides a portable handle add-on module for physicians to manipulate the bronchoscope manually without using the robotic support system. For example, the handle portion of the robotic bronchoscope may have a unified interface allowing the robotic bronchoscope to be releasably connected to an instrument driving mechanism of a robotic support system, a portable handle device, a controller or user interface device, a modular wireless communication device and various others.

Figure 21A:
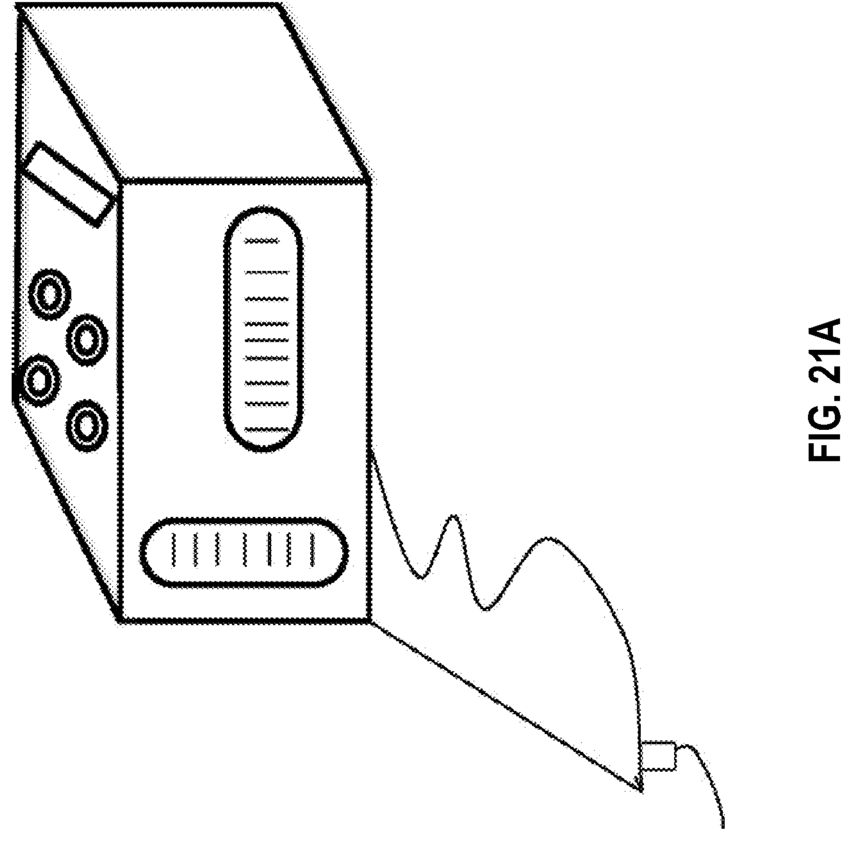
FIG. 21A shows an example of a portable handle add-on module.

An example of a portable handle add-on module design is shown below in FIG. 21A. The module may have an electrical interface which connects to the proximal board inside the handle. The electrical interface may include signal connections. A plurality of matching mechanical pulleys may engage the capstans of the handle. Two or more may knobs allow the combination motion of all pulleys which can articulate the robotic bronchoscope distal tip. The add-on module may be connected to the user interface through wired connection, wirelessly connection or a combination of both. For example, a communication module such as a WiFi chip inside the module may broadcast video from the bronchoscope to multiple portable displays. The portable handle add-on module may comprise a power source such as a battery to provide a backup power source to the camera in addition to the cable in the handle. Alternatively or in addition to, a cable/wired communication can be used.

Figure 21B:
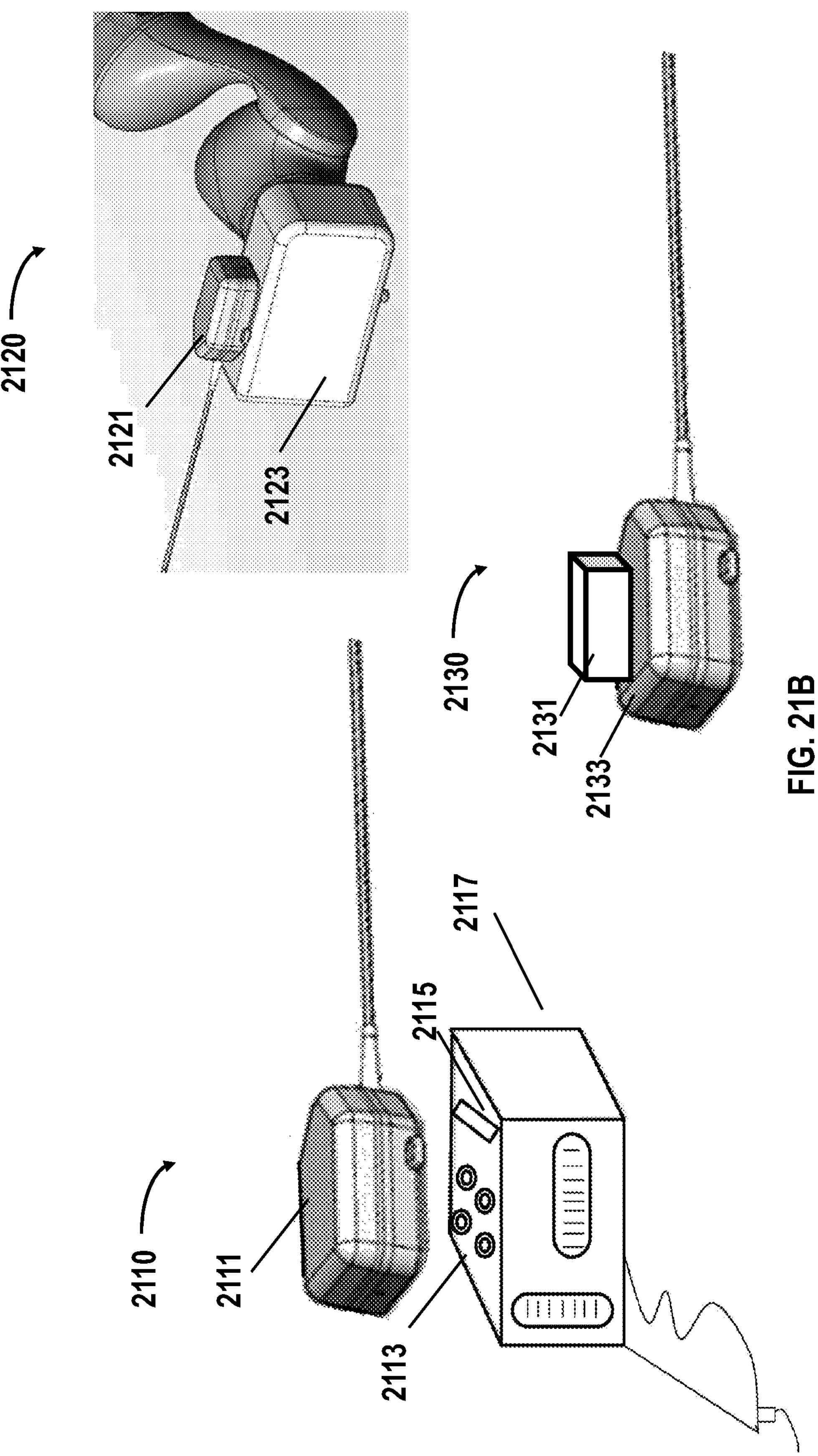
FIG. 21B shows various examples of a robotic bronchoscope used in conjunction with various systems, devices and modules.

As mentioned above, the robotic bronchoscope may be designed to be capable of interfacing with external devices in a plug-and-play fashion. FIG. 21B shows various examples of a robotic bronchoscope used in conjunction with various systems, devices and modules. In a first scenario 2110, the handle portion 2111 of the robotic bronchoscope may be connected to a portable handle add-on module 2117 via a mechanical and electrical interface as described above. For example, the portable handle-add-on module may provide a mechanical interface comprising driving elements (e.g., motors) 2113 that are actuated to rotationally drive a set of pull wires of the catheter. In some cases, the portable handle add-on module 2117 may also provide an electrical interface 2115 in electrical communication with the proximal board in the handle portion 2111 for transmitting sensor data and/or control signals. In some embodiments, the same robotic bronchoscope 2121 may be releasably connected to and switch between a portable handle add-on module and a robotic support system as shown in the example 2120. The robotic bronchoscope may have a unified interface allowing a convenient switch between an instrument driving mechanism 2123 and a portable handle add-on module 2117. In some embodiments, the instrument driving mechanism, the portable handle add-on module or both may provide a mechanical interface only. As shown in the scenario 2130, a modular wireless communication device 2131 (e.g., WiFi module) may be provided and the modular wireless communication device 2131 (e.g., WiFi module) can be releasably coupled to the handle portion 2133 to extend the electrical communication capability of the robotic bronchoscope. For example, the modular wireless communication device 2131 (e.g., WiFi module) may be in electrical communication with the handle portion for transmitting sensor data to an external device and/or receiving control signals from an external control system. This may advantageously allow the robotic bronchoscope to be used or integrated with existing robotic systems, user devices or surgical systems regardless the electrical communication capability of the underlying systems.

Portable Robotic Cone Beam CT

Conventional cone beam CT machines may have the emitter and receiver panel on the same mechanical structure with a C shape or O shape. The connection between emitter and receiver panel can cause the cone beam CT to be large in size. This oversize design poses limitations on the use case and takes a lot of space in rather tight operating room.

Described herein, is a design to decouple the mechanical connection between the emitter and the receiver panel. FIG. 22 shows an example portable robotic cone beam CT. The emitter and receiver panel can be mounted on two separate robot arms separately, as shown in the example of FIG. 22. When in use, the two robots can move in the same coordinate system. A control algorithm may ensure that the two robots are moving in a synchronous motion.

In addition, for patients gating motion, i.e. breathing, additional external sensors—i.e. IMU, EM, or image sensors—can be added to track the motion of the patient. The position changes in patient can be tracked using sensors such as IMU, EM, or image sensors. The sensory signals can be used to command the two robot arms. In some cases, either or both of the robot arms can be moving to track the patient motions, which essentially make the emitter and receiver stationary to the patient motion for the region of interest (ROI) when tracking. The ROI may comprise a target site or a target location that can be determined automatically by the system or manually by a physician. The tracking can also be done using other mechanisms such as but not limited to external camera and one or a plurality of trackers on the patient body.

It should be understood by the person skilled in the art that cone beam CT is a nonlimiting example. The design described herein may be used for other imaging modalities such as a fluoroscopic machine, classic CT machine, and MRI machine.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A robotic flexible endoscopic apparatus to be inserted into a subject comprising:

a disposable flexible elongate member comprising:

a proximal end and a distal end, wherein the proximal end is removably attached to a robotic arm via a handle, wherein the distal end is integrated with an imaging device, a position sensor and an illumination device;

and a flexible bending section that is articulated by one or more pull wires, wherein the handle is configured to removably couple to an instrument driving mechanism attached to the robotic arm, and wherein at least a portion of the disposable flexible elongate member is prevented from buckling by an anti-buckling device, wherein a distal end of the anti-buckling device is configured to travel along a linear trajectory prior to inserting the disposable flexible elongate member into the subject, wherein an alignment feature is configured to align the anti-buckling device in a collapse state to a connector that is not located on the subject thereby ensuring the linear trajectory, and wherein upon alignment, the anti-buckling device is extended such that the distal end of the anti-buckling device travels along the linear trajectory until it is connected to the connector.

2. The robotic flexible endoscopic apparatus of claim 1, wherein the distal end of the disposable elongate member comprises a structure to receive the imaging device, the position sensor, and the illumination device.

3. The robotic flexible endoscopic apparatus of claim 1, wherein the imaging device, the position sensor, and the illumination device are arranged into a compact configuration.

4. The robotic flexible endoscopic apparatus of claim 1, wherein the handle includes one or more components configured to process image data, provide power to the imaging device, the position sensor and the illumination device, or establish communication with an external device.

5. The robotic flexible endoscopic apparatus of claim 1, wherein the handle comprises an interface configured to couple the handle to the instrument driving mechanism.

6. The robotic flexible endoscopic apparatus of claim 5, wherein the interface includes an electrical interface and a mechanical interface and wherein the mechanical interface is configured to releasably couple the handle to the instrument driving mechanism.

7. The robotic flexible endoscopic apparatus of claim 1, wherein the alignment feature is configured to assist in creating the alignment between the instrument driving mechanism and the connector at the target site prior to connecting the anti-buckling mechanism to the instrument driving mechanism.

8. The robotic flexible endoscopic apparatus of claim 1, wherein the alignment feature includes a magnetic component, a laser or a click button.

9. The robotic flexible endoscopic apparatus of claim 1, wherein the anti-buckling mechanism comprises a series of connected cylinders each including a lip structure.

10. The robotic flexible endoscopic apparatus of claim 9, wherein the lip structure of each cylinder has a hole with same diameter.

11. The robotic flexible endoscopic apparatus of claim 1, wherein both the handle and the disposable elongate member are single-use.

12. The robotic flexible endoscopic apparatus of claim 1, wherein the one or more pull wires are individually attached to the bending section according to a selected configuration pattern.

13. The robotic flexible endoscopic apparatus of claim 12, wherein a control of the articulation of the robotic flexible endoscopic apparatus is updated based at least in part on a mapping relationship between the selected configuration pattern and an updated configuration pattern upon a change of state of the one or more pull wires.

14. The robotic flexible endoscopic apparatus of claim 1, wherein the alignment feature comprises a mechanical alignment feature.

15. The robotic flexible endoscopic apparatus of claim 14, wherein at least part of the mechanical alignment feature is located on the connector.

16. A robotic endoscopic system comprising the robotic flexible endoscopic apparatus of claim 1 and a user control interface device configured for a user to control a movement of the robotic flexible endoscopic apparatus.

17. The robotic endoscopic system of claim 16, wherein the user control interface device is personalized with aid of a machine learning algorithm trained model that is trained based on past user behavior.

18. The robotic endoscopic system of claim 16, further comprising a display interface configured to display image data captured by the imaging device overlaid with virtual renderings of one or more anatomical structures.

19. The robotic endoscopic system of claim 18, wherein a display of the virtual renderings of the one or more anatomical structures is selectively enabled or disabled by the user via the display interface.

* * * * *